United States Patent
Anderson et al.

(10) Patent No.: US 7,104,949 B2
(45) Date of Patent: Sep. 12, 2006

(54) SURGICAL ARTICLES FOR PLACING AN IMPLANT ABOUT A TUBULAR TISSUE STRUCTURE AND METHODS

(75) Inventors: Kimberly A. Anderson, Eagan, MN (US); Brian P. Watschke, Eden Prairie, MN (US); Randy L. Morningstar, Brooklyn Park, MN (US); Timothy A. Bachman, St. Paul, MN (US); Johann J. Neisz, Coon Rapids, MN (US)

(73) Assignee: AMS Research Corporation, Minnetonka, MN (US)

( * ) Notice: Subject to any disclaimer, the term of this patent is extended or adjusted under 35 U.S.C. 154(b) by 715 days.

(21) Appl. No.: 10/233,349

(22) Filed: Aug. 30, 2002

(65) Prior Publication Data

US 2003/0055313 A1    Mar. 20, 2003

Related U.S. Application Data

(60) Provisional application No. 60/325,870, filed on Sep. 28, 2001, provisional application No. 60/316,552, filed on Aug. 31, 2001.

(51) Int. Cl.
*A61F 2/02* (2006.01)
(52) U.S. Cl. ...................................................... 600/30
(58) Field of Classification Search ............ 600/29–32, 600/37; 606/151, 153, 155, 158; 623/1.14, 623/1.23; 604/16–18, 500, 507–509, 513, 604/514
See application file for complete search history.

(56) References Cited

U.S. PATENT DOCUMENTS

| | | | |
|---|---|---|---|
| 1,449,087 A | 3/1923 | Bugbee | |
| 3,470,875 A | 10/1969 | Johnson | |
| 3,763,860 A | 10/1973 | Clarke | |
| 3,946,740 A | 3/1976 | Bassett | |
| 4,164,225 A | 8/1979 | Johnson et al. | |
| 4,686,962 A | 8/1987 | Haber | |
| 4,923,461 A | 5/1990 | Caspari et al. | |
| 4,935,027 A | 6/1990 | Yoon | |
| 4,938,760 A | 7/1990 | Burton et al. | |
| 5,007,894 A | 4/1991 | Enhorning | |
| 5,167,614 A * | 12/1992 | Tessmann et al. | 623/1.15 |
| 5,234,409 A | 8/1993 | Goldberg et al. | |
| 5,256,133 A | 10/1993 | Spitz | |
| 5,431,666 A | 7/1995 | Sauer et al. | |
| 5,527,321 A | 6/1996 | Hinchliffe | |
| 5,647,836 A | 7/1997 | Blake, III et al. | |
| 5,674,230 A | 10/1997 | Tovey et al. | |
| 5,697,931 A | 12/1997 | Thompson | |
| 5,728,107 A | 3/1998 | Zlock et al. | |
| 5,730,747 A | 3/1998 | Ek et al. | |
| 5,741,279 A | 4/1998 | Gordon et al. | |
| 5,800,524 A * | 9/1998 | Borghi | 623/1.13 |
| 5,813,411 A * | 9/1998 | Van Bladel et al. | 128/898 |

(Continued)

OTHER PUBLICATIONS

Burch, Urethrovaginal Fixation to Cooper's Ligament for Correction of Stress Incontinence, Cystocele, and Prolapse, Am. J. Obst. & Gyn, vol. 81 (No. 2), pp. 281-290 (1961).

(Continued)

*Primary Examiner*—Samuel G. Gilbert
(74) *Attorney, Agent, or Firm*—Jose W. Jimenez

(57) ABSTRACT

A minimally invasive surgical instrument for placing an implantable article about a tubular tissue structure is disclosed. The surgical instrument is particularly useful for treating urological disorders such as incontinence. Surgical methods using the novel instrument are also described.

4 Claims, 19 Drawing Sheets

U.S. PATENT DOCUMENTS

| | | | |
|---|---|---|---|
| 5,871,488 | A | 2/1999 | Tovey et al. |
| 5,997,554 | A | 12/1999 | Thompson |
| 6,030,337 | A | 2/2000 | Grant et al. |
| 6,048,351 | A | 4/2000 | Gordon et al. |
| 6,056,771 | A | 5/2000 | Proto |
| 6,068,591 | A | 5/2000 | Bruckner et al. |
| 6,093,194 | A * | 7/2000 | Mikus et al. ............... 606/108 |
| 6,149,667 | A | 11/2000 | Hovland et al. |
| 6,387,040 | B1 | 5/2002 | Grant et al. |
| 6,416,522 | B1 * | 7/2002 | Strecker ..................... 606/143 |
| 6,517,566 | B1 | 2/2003 | Hovland et al. |
| 2002/0072694 | A1 | 6/2002 | Snitkin et al. |
| 2002/0078964 | A1 | 6/2002 | Kovac et al. |

OTHER PUBLICATIONS

CAPIO™ CL Transvaginal Suture Capturing Device, Boston Scientific, Microvasive, 4 pages (2000).

CAPIO™ Suture Capturing Device, Boston Scientific, Microvasive, 4 pages (1998).

Das et al., Laparoscopic Colpo-Suspension, Journal or Urology, vol. 154, pp. 1119-1121 (1995).

Gilja et al., The Modified RAZ Bladder Neck Suspension Operation (Transvaginal Burch), Journal of Urology, vol. 153, pp. 1455-1457 (May 1995).

Holschneider et al., A Modified Pereyra Procedure in Recurrent Stress Urinary Incontinence: A 15-Year Review, Obstetrics & Gynecology, vol. 83 (No. 4), pp. 573-578 (1994).

Horbach et al., a Suburethral Sling Procedure With Polytetrafluoroethylene for the Treatment of Genuine Stress Incontinence in Patients With Low Urethral Closure Pressure, J. Obstetrics & Gynecology, vol. 71 (No. 4), pp. 648-652 (Apr. 1998).

Marshall et al. The Correction of Stress Incontinence by Simple Vesicourethral Suspension, Surgery, Gynecology and Obstetrics, vol. 88, pp. 509-518 (1949).

Morgan et al., The Marlex Sling Operation for the Treatment of Recurrent Stress Urinary Incontinence: A 16 Year Review, Am. J. Obstet. Gynecol., vol. 151 (No. 2), pp. 224-227 (Jan. 1985).

Pereyra, A Simplified Surgical Procedure for Correction of Stress Incontinence in Women, West.J.Surg., Obst. & Gynec, pp. 223-226, (Jul. Aug. 1959).

Stamey, Endoscopic Suspension of the Vesical Neck for Urinary Incotinence in Females, Ann. Surg., vol. 192 (No. 4), pp. 465-471 (Oct. 1980).

* cited by examiner

SURGICAL ARTICLES FOR PLACING AN IMPLANT ABOUT A TUBULAR TISSUE STRUCTURE AND METHODS

CROSS REFERENCE TO RELATED APPLICATIONS

The present application claims priority to U.S. provisional patent application No. 60/325,870, filed Sep. 28, 2001, and U.S. provisional patent application No. 60/316,552, filed Aug. 31, 2001.

BACKGROUND

Examples of surgical instruments for soft tissue repair or manipulation are disclosed in U.S. Pat. Nos. 1,449,087; 3,470,875; 3,763,860; 3,946,740; 4,164,225; 4,923,461; 4,935,027; 5,527,321; 5,431,666; 5,674,230; 5,728,107; 5,730,747, 5,741,279; 5,871,488; 6,056,771 and 6,084,351.

The Capio™ CL Transvaginal Suture Capturing Device, and the Capio™ Suture Capturing Device are available from Boston Scientific, of Natick, Mass. These devices are capable of passing a suture through tissue.

The ArthroSew™ Disposable Suturing Device is available from Surgical Dynamics (U.S. Surgical), of Norwalk, Conn. The Veronikis Ligature Carrier™ is available from Marina Medical of Hollywood, Fla. The device is designed for sacrospinous ligature suspension of prolapsed vaginal vault. The device includes a needle with an eyelet and two clamp fingers. The clamp fingers do not include a mechanism for positively capturing the suture once it is passed through the tissue. As a result, an independent device (e.g. a suture retrieval hook) is required for use with this device to retrieve a suture that is passed through tissue.

Loss of bladder control is a condition known a urinary incontinence. Surgical procedures can be used to completely restore continence in some instances. The literature reports hundreds of different surgical procedures or variations designed to treat incontinence.

Surgical procedures include anterior colporrhaphy procedures, colposuspension procedures, and needle suspension procedures. Colposuspension procedures seek to place the urethra in a high retropubic position. The Marshall-Marchetti-Krantz procedure and the Burch procedure are examples of colposuspension procedures. The Marshall-Marchetti-Krantz procedure places sutures at the urethrovesical junction to the periosteum of the pubic bone. See Marshall et al., *The Correction of Stress Incontinence By Simple Vesicourethral Suspension;* Surg. Gynecol. Obstet. Vol. 88, Pps. 509–518 (1949).

With the Burch procedure, sutures are placed at the urethrovesical junction to Cooper's ligament. See Gilja et al., *A Modified Raz Bladder Neck Suspension Operation (Transvaginal Burch),* J. of Urol. Vol. 153, Pps. 1455–1457 (May 1995). A significant abdominal incision is associated with the Marshall-Marchetti-Krantz procedure. The Burch procedure has been performed abdominally, vaginally and laparoscopically. See Burch, *Urethrovaginal Fixation to Cooper's Ligament for Correction of Stress Incontinence, Cystocele, and Prolapse,* Am. J. Obst. & Gynecology, vol. 81 (No. 2), Pps. 281–290 (February 1961); and Das et al., *Laparoscopic Colpo-Suspension,* J. of Urology, vol. 154, Pp. 1119–1121 (1995).

Needle suspension procedures elevate the urethra retropubically. They include Pereyra, Stamey, Raz, Gittes, Muszani and Vesica procedures. These procedures (except the Vesica procedure) place sutures transvaginally at the urethrovesical junction and are sutured to the abdominal wall through two small abdominal incisions. See Stamey, *Endoscopic Suspension of the Vesical Neck for Urinary Incontinence in Females,* Ann. Surgery, pp. 465–471, October 1980; Pereyra, *A Simplified Surgical Procedure for the Correction of Stress Incontinence in Women,* West. J. Surg., Obstetrics & Gynecology, pp. 243–246, July–August 1959; Holschneider et al., *A Modified Pereyra Procedure In Recurrent Stress Urinary Incontinence: A 15-Year Review,* Obstetrics & Gynecology, vol. 83, No. 4 Pps. 573–578 (1994). The Vesica procedure includes an abdominal incision where bone anchors are driven into the top of the pubic bone and sutures attached to the bone anchors are placed at the urethrovesical junction.

An anterior colporrhaphy procedure seeks to elevate and support the bladder neck within the abdominal zone of pressure and allow posterior compression of the proximal urethra against the pubic symphysis. A complication associated with these procedures is voiding difficulties, possibly due to the resultant geometry of the urinary tract.

Another surgical procedure for treating incontinence is a sling procedure, the first of which was the Goebel-Stoeckel-Frannenheim procedure. There are two general types of sling procedures. The first type of sling procedure utilizes bone screws and associated sutures to anchor a sling (e.g. on a posterior portion of the pubic bone). A commercial example of a bone screw sling procedure is a surgical procedure that utilizes the In-Fast Sling System, available from American Medical Systems of Minnetonka, Minn.

The second type of sling procedure is a minimally invasive surgical method involving the placement (e.g. by the use of a Stamey needle or other ligature carrier) of a sling to stabilize or support the bladder neck or urethra. See Horbach et al., *A Suburethral Sling Procedure With Polytetrafluoroethylene For the Treatment of Genuine Stress Incontinence In Patients With Low Urethral Closure Pressure,* J. Obstetrics & Gynecology, vol. 71, No. 4, Pps. 648–652 (April 1998); and Morgan et al., *The Marlex Sling Operation For the Treatment of Recurrent Stress Urinary Incontinence: A 16 Year Review,* Am. J. Obstet. Gynecol., vol. 151, No. 2, Pps. 224–227 (January 1985).

The slings described above differ in the type of material, sutures and points of anchoring based on the procedure being performed. In some cases, the sling is placed under the bladder neck and secured via suspension means (such as bone anchors or screws) through a vaginal incision. Bone anchors or screws raise the specter of bone infection, necrosis and other complications, although such complications are rare.

The second type of sling procedure (pubovaginal sling procedures that do not include bone anchors) anchor slings in the abdominal or rectus fascia. These types of procedures involve puncturing the abdominal wall of the patient to pass a needle. Complications associated with sling procedures are rare, but they include urethral obstruction, infection, development of de novo urge incontinence, bladder perforation, hemorrhage, prolonged urinary retention, and damage to surrounding tissue (e.g. caused by sling erosion). The likelihood of complications due to abdominal incisions varies and depends on the particular surgical procedure.

U.S. Pat. Nos. 6,030,337 and 6,387,040 disclose urinary continence devices and methods for treating incontinence. In some embodiments, a medical device is placed within the urethra.

Other examples of surgical instruments for addressing incontinence or other urological disorders are disclosed in U.S. Pat. Nos. 4,686,962; 4,938,760; 5,234,409; 5,256,133; 5,647,836; 5,697,931; 5,997,554; 6,068,591 and 6,149,667.

BRIEF SUMMARY

The present invention is directed to minimally invasive surgical instruments for use in soft tissue reconstruction, manipulation, connection and/or repairs, particularly those encountered in urological and gynecological applications. The instruments are particularly suitable for use in soft tissue repair such as pelvic floor repair and reconstruction procedures. The instruments are particularly suitable for treating incontinence.

Examples of particular applications for surgical instruments according to the present invention include, but are not limited to procedures for addressing gastroesophageal reflux disease (GERD), urinary incontinence, paravaginal defect repairs, venous flow restriction for erectile dysfunction, fecal incontinence, obesity, arterial support, aneurysm support, repairs of cystoceles, rectoceles, and enteroceles, and prolapse repair.

The repairs of the present invention may be achieved without substantially changing the orientation of the patient's anatomy to avoid, in the case of an incontinence procedure, post-surgical voiding difficulties brought about by the change in the orientation of the natural body passageway (e.g. the urethra or urethral meatus). In some embodiments of the present invention, urinary incontinence may be treated without the need for a significant abdominal incision or, in some embodiments, a small vaginal incision or puncture.

In one aspect, the present invention comprises a surgical device for placing an implantable article about a tubular tissue structure, such as the urethra. The device comprises an elongate tubular tissue structure immobilizer sized and shaped to be placed within the tubular tissue structure, an implantable article deployment member movable about the immobilizer between a retracted position and an extended position; an actuator for moving the implantable article deployment member between the retracted and extended positions; an holder for retaining the implantable article in the patient once the implantable article deployment member moves to the extended position; and a separator for extricating the implantable article from the surgical device.

In one embodiment, the implantable article deployment member is capable of moving along a substantially helical path, in other embodiments, the path is non-helical.

In one embodiment, the retracted position of the implantable article deployment member is situated within the tubular tissue structure and the extended position is located external to the tubular tissue structure. In another embodiment, the path of the implantable article deployment member is entirely external to the tubular tissue structure (urethra) without traversing the urethra. In this embodiment, the surgical device is capable of implanting the implantable article without piercing the tubular tissue structure.

The surgical device may optionally include features such as a means for collapsing the tubular tissue structure about the immobilizer (e.g. a vacuum component), or an inflatable member (e.g. balloon) for positioning the surgical device relative to the tubular tissue structure.

The actuator may comprise any suitable mechanism such as rotatable members, linearly movable members or combinations thereof. In one embodiment, the actuator may comprise a slidable guide member with a helical cam groove and a cam follower associated with the implantable article deployment member. In another embodiment, the actuator may comprise gears, detents and grooves. The actuator may also comprise a gear and a predetermined shaped gear track. Combinations of such actuator elements are also within the scope of the present invention.

Preferably, the path of the implantable article deployment member is substantially semi-circular about an axis of the immobilizer.

The actuator may comprise a variety of different type mechanisms. Generally speaking, mechanical linkages including gears, cams, cam followers, gear tracks, and splines are suitable for incorporation into the surgical instrument as the actuator. Other actuators such as pneumatic actuators are also contemplated as within the scope of the present invention.

In another embodiment, the implantable article deployment member is composed of a shape memory material capable of resiliently deflecting into a predetermined shape during movement from the retracted toward the extended position.

Some embodiments of the surgical instrument of the present invention are transurethral devices without any structure projecting into the vagina. Other embodiments include a portion for insertion in the vagina.

Surgical instruments according to the present invention may implant a wide variety of implantable articles. The implantable articles may be constructed from synthetic or non-synthetic elements or combinations thereof. The implantable articles may be constructed from resorbable, absorbable or substantially permanent implant materials. The implantable article may be rigid (e.g. a spring like structure) or non-rigid (e.g. a suture-like structure).

In one embodiment, the implantable article comprises a suture having a dart associated with a leading end thereof. The dart has a shoulder surface. The implantable article deployment member has an internal passageway affording passage of the suture, and a distal end sized and shaped to engage the shoulder surface of the dart to drive the dart along the path of the implantable article deployment member. In this embodiment, the holder comprises dart receiving surfaces in the surgical instrument, for engaging surfaces of the dart to hold the dart and suture in the extended position while the implantable article deployment member retracts to the retracted position leaving the suture in the extended position.

The separator may comprise a wide variety of structures. For example, it may comprise a rod movable within an internal passageway of the implantable article deployment member to eject a pre-cut or pre-sized implantable article (e.g. a coil of wire) from the surgical device. In another embodiment, the separator may comprise a cutter for cutting the implantable article in situ after the implantable article deployment member moves from the retracted to the extended position.

In another aspect, the present invention comprises a surgical method for placing an implantable article about a tubular tissue structure. The surgical procedure may be for general surgical purposes discussed in greater detail below. The surgical instruments are particularly suitable for treating incontinence. In embodiment, the method comprises the steps of a) inserting a surgical device with an implantable article situated therein into a urethra, b) moving the implantable article from a position within the urethra to a position at least substantially external to the urethra; c) separating the implantable article from the device, and d) removing the surgical device from the urethra leaving the implantable article situated about the urethra. The procedure has, among other advantages, the advantage of treating incontinence without requiring an incision in the vagina or abdomen of the patient.

In another aspect, the method comprises the steps of: a) providing a surgical device having an immobilizer and a stabilizer, and a implantable article deployment member movable about the immobilizer between a retracted position and an extended position; b) inserting the immobilizer into the urethra and the stabilizer within the vagina; c) moving the implantable article deployment member along a path that is substantially external to the urethra from the retracted to the extended position; d) retracting the implantable article deployment member from the extended to the retracted position leaving the implantable article situated about the urethra; e) separating the implantable article from the device; and f) removing the surgical device from the patient's body. This procedure has the advantage of treating the incontinence without substantially changing the patient's urinary tract orientation to avoid post implantation voiding difficulties

BRIEF DESCRIPTION OF THE DRAWINGS

Other features and advantages of the present invention will be seen as the following description of particular embodiments progresses in conjunction with the drawings, in which:

FIGS. 1 through 4 are schematic illustrations of an apparatus and sequential process according to an aspect of the present invention wherein, FIG. 1 is a schematic illustration of a surgical device deployed within the bladder and urethra;

FIG. 2 is a schematic illustration of the surgical device with an inflatable member inflated, a vacuum feature deployed to collapse the urethra, and with an implantable member deployment element retracted within the urethra;

FIG. 3 is a schematic illustration of the surgical device with the implantable member deployment element extended from the position of FIG. 2 to a position outside the urethra to deploy an implantable member about the urethra;

FIG. 4 is a schematic illustration after the implantable member deployment element has been retracted back within the urethra, the inflatable member deflated, the vacuum released, and the surgical device withdrawn from the bladder and urethra, leaving an implantable member deployed in a helical orientation about the urethra;

FIGS. 13*a* through 16*b* sequentially illustrate movement of elements of an embodiment of surgical instrument according to the present invention, wherein:

FIG. 13*a* is a perspective view illustrating an implantable member deployment member in a retracted position;

FIG. 16*b* is an end view of the components of FIG. 16*a*;

DETAILED DESCRIPTION

The following description is meant to be illustrative only and not limiting. Other embodiments of this invention will be apparent to those of ordinary skill in the art in view of this description.

FIGS. 1 through 4 are schematic illustrations of a surgical device for placing an implantable article about a tubular tissue structure, such as a patient's urethra U. The bladder neck is situated between the patient's bladder B and urethra U.

Figure 3:
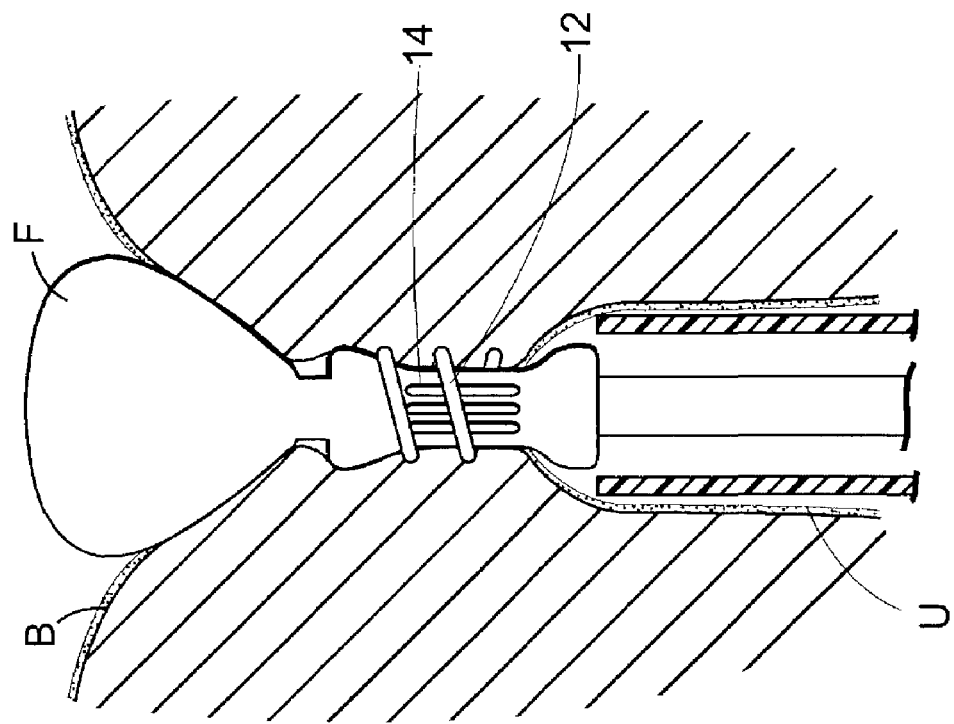

The surgical device includes an inflatable member F, a means for collapsing the tubular tissue structure (in this embodiment a vacuum element 14) about an immobilizer (the tubular structure between the vacuum ports), and an implantable article deployment member 12 movable between a retracted position (FIG. 1) and an extended position (FIG. 3).

Figure 1:
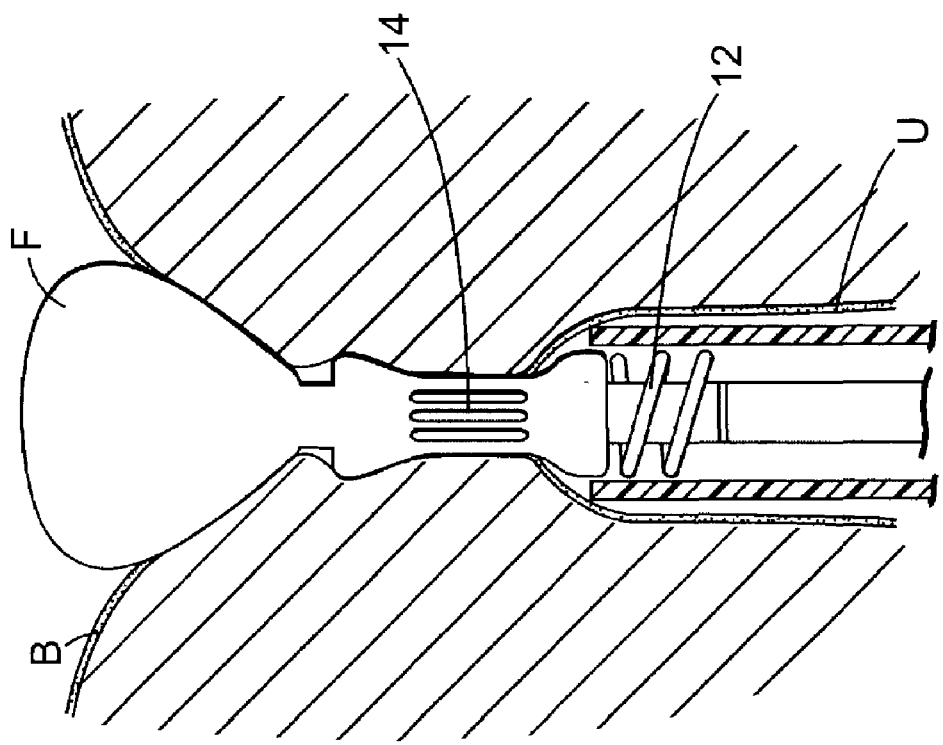

FIG. 1 shows the surgical device after it is inserted transurethrally so that portions are deployed within the bladder B and urethra U.

Figure 2:
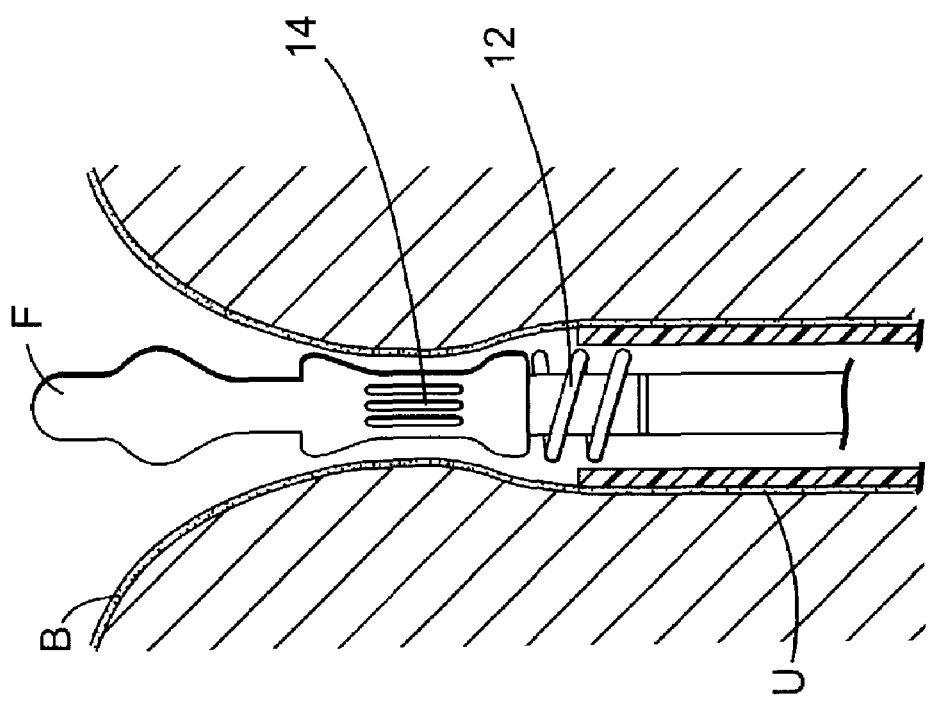

FIG. 2 shows the inflatable member F inflated, the vacuum element activated to collapse the urethra U about the device, and with an implantable member deployment element 12 retracted within the urethra U. The inflatable member F or similar landmarking component positions the vacuum ports of the device in a predetermined position, preferably near the mid urethra. Next, a vacuum is applied and the urethra U is collapsed about the device.

FIG. 3 shows the implantable member deployment element 12 extended from the position of FIG. 2 to a position outside the urethra U to deploy an implantable article 13 about the urethra U. While holding the vacuum, an implantable article 13 is advanced forward (e.g. by a screwing motion). The implantable member deployment member 12 preferably moves along a substantially helical path, but other paths such as circular, elliptical or semicircular are also within the present invention.

Preferably, the present invention places the implantable article 13 outside the urethra U. Comparing FIGS. 2 to 3, the retracted position of the implantable article deployment member 12 is situated within the urethra U and the extended position is located substantially external to the urethra U. The leading end of the implantable article 13 or deployment member 12 penetrates the urethra wall, winds around the urethra U as the implantable article deployment member 12 is further advanced.

Preferably, the implantable article 13 is associated with the implantable article deployment member 12 so that, at the end of the placement cycle, a portion of the deployment member 12 penetrates the urethral wall. As a result, when the vacuum is released and the deployment member 12 is retracted, the deployment member 12 is disassociated with the implantable article 13. This helps ensure that the implantable article 13 is substantially completely seated on the outside perimeter of the urethra U. Optionally, an ejector rod may be place within the deployment member 12 to ensure separation of the implantable article 12 from the surgical device.

Figure 4:
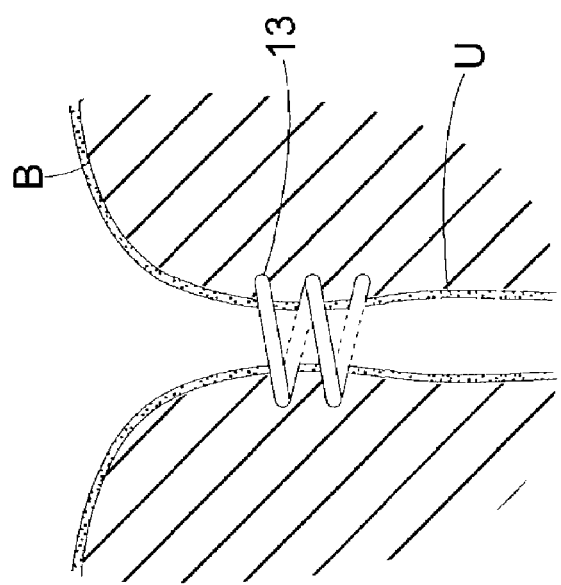

FIG. 4 is a schematic illustration after the implantable member deployment element 12 has been retracted back within the urethra U, the inflatable member F deflated, the vacuum released, and the surgical device withdrawn from the bladder B and urethra U leaving an implantable member 13 deployed in a helical orientation about the urethra U.

In the embodiment shown in FIGS. 1–4, the implantable article 13 is preferably loosely placed surrounding or about the mid urethra. The implantable article 13 is preferably sized and shaped to loosely seat around the peripheral tissue of the urethra. The implantable article 13 preferably should not constrict the urethra. Preferably, the implantable article 13 may have between 0.5 and 4 windings, preferably between about 1.5 to 2 windings. Alternatively a plurality of implantable members may be placed about the urethra during the surgical procedure.

The implantable article 13 is preferably constructed from a material that affords easy radial expansion (e.g. by between about 10 and about 20%) and above that drastically increases in resistance to deformation particularly radial expansion. It is constructed of a medical grade material, preferably without sharp components (e.g. ends) to avoid erosion. Optionally, the implantable article could be constructed from bioresorbable materials in whole or in part. Potentially, scarring may be exploited to render permanent presence of all or a part of the implantable article 13 to be unnecessary. Although not intending to be bound by any one theory, one reason that the present invention is believed to be quite useful is the diametrical expansion of the urethra U during a stress event.

It is believed that the effective treatment of female urinary stress incontinence may be achieved by slightly elevating intraurethral pressure at the mid urethra. The elevation should be minimal in order to offset rises in vesical pressure during a stress event (e.g. laughing or coughing). The urethral and vesical relationship is discussed in Lazarevski, *Biomechanics of Urinary Stress Incontinence Surgery— Theory of the Non-Permanently Acting Suburethral Supportive Structure,* Int. Urogynecol. J., (2000) 11:377–385.

Restricting urethral diameter during a stress event is a way to elevate intraurethral pressure and gain continence. Restricting the urethral diameter during a stress event is believed to decrease outflow of urine.

Elevation of mid urethral pressure is greatly determined by the structural integrity of the external sphincter. The inability to contract or inability to sustain a fixed diameter of the external sphincter results in a loss of urine during a stress event.

In other embodiments of the present invention, other implantable articles may be used. The implantable article may comprise synthetic or non-synthetic materials or hybrids or combinations thereof. The implantable article can comprise a material suitable for correcting pelvic floor disorders such as a cystocele or a rectocele or a prolapse. The implantable material may optionally comprise a suture or sling material. For example, the suture may comprises a polypropylene monofilament suture attached to a stainless steel (e.g. 17-4 PH 630 SST) dart with conical tip with an included angle of about 56 degrees.

Suitable non-synthetic materials for the implantable article include allografts, xenografts, homografts, heterografts, autologous tissues, cadaveric fascia and fascia lata. The implantable article may include living tissue, processed tissue, tissue-engineered implants, tissue scaffolding and combinations thereof.

Suitable synthetic materials include polymerics, and plastics and any combination of such materials. Commercial examples of materials for implantable articles include Mersilene™, Teflon™, Gore-Tex™, Silastic™, Marlex™, Prolene™, and Vaskutek™. Other examples of suitable materials include those disclosed in U.S. patent application Ser. No. 09/939,098 filed Aug. 24, 2001, and Published U.S. Patent Application No. US-2002-0107430-A1. Specific examples of synthetic implantable articles include absorbable and non-absorbable materials such as polypropylene, polyethylene, nylon, PLLA and PGA.

In other embodiments, the implantable article may comprise a biofoam, tissue adhesive, or tissue sealant. The compositions of such implantable articles can be absorbable or non-absorbable, permanent or they may be temporary, designed to last for a predetermined or therapeutically effective amount of time. They may be in liquid, gaseous, solid, gel or colloidal form. The biofoam may include biological, synthetic, nonsynthetic, synergraft, Xenograft, and/or cadaveric elements.

As examples, not intended to be limiting, the foam, tissue adhesive and/or sealant and/or implantable composition may comprise an adhesive utilizing human or bovine albumen, a fibrin adhesive/sealant such as the Tisseel® Fibrin Sealant available from Baxter Healthcare Corp. of Deerfield, Ill. Other examples include acrylate adhesives described, for example, in U.S. Pat. Nos. 6,001,345, 6,214,332, and 6,248,800; and collagen including adhesives, sealants, wound dressings and implantable compositions. Examples of suitable foams, adhesive/sealant/implantable compositions are described, in U.S. Pat. Nos. 4,216,204; 4,455,302; 4,759,354; 4,837,024; 4,950,699; 5,081,106; 5,116,620; 5,196,185; 5,350,798; 5,370,698; 5,385,606; 5,436,361; 5,613,982; 5,632,778; 5,741,782; 5,843,182; 5,899,937, 5,938,681; 6,136,341 and 6,245,083 and European Pat. Document Nos. 530 982 and 450 671.

Commercially available examples of tissue adhesives, tissue sealants and implantable compositions include those available from Collagen Corp., Baxter Healthcare Corp. of Deerfield, Ill.; Focal, Inc., U.S. Surgical/Tycos; Genzyme; Ethicon, Inc. (J&J) of Ohio; PPL Therapeutics Ltd. (U.K.), Tissuemed Ltd. (U.K.) and MedLogic Global Corp. of Colorado Springs, Colo.

In embodiments where the implantable articles are sutures, the sutures may comprise any suitable sutures including monofilament and braided sutures. The sutures may be constructed from a resorbable material or a substantially permanent material such as polyester. A commercial example of an absorbable suture is the Bondek® Braided Synthetic Absorbable PGA (polyglycolic acid) Suture, available from Genzyme. In another embodiment, the implantable article may be part of an assembly that includes a needle-like leading end. Commercial examples of such assemblies include Surgilene Monofilament Polypropylene Suture assemblies available from Davis & Geck, and the Prolene Monofilament Polypropylene Sutures available from Ethicon, Inc.

Figure 5:
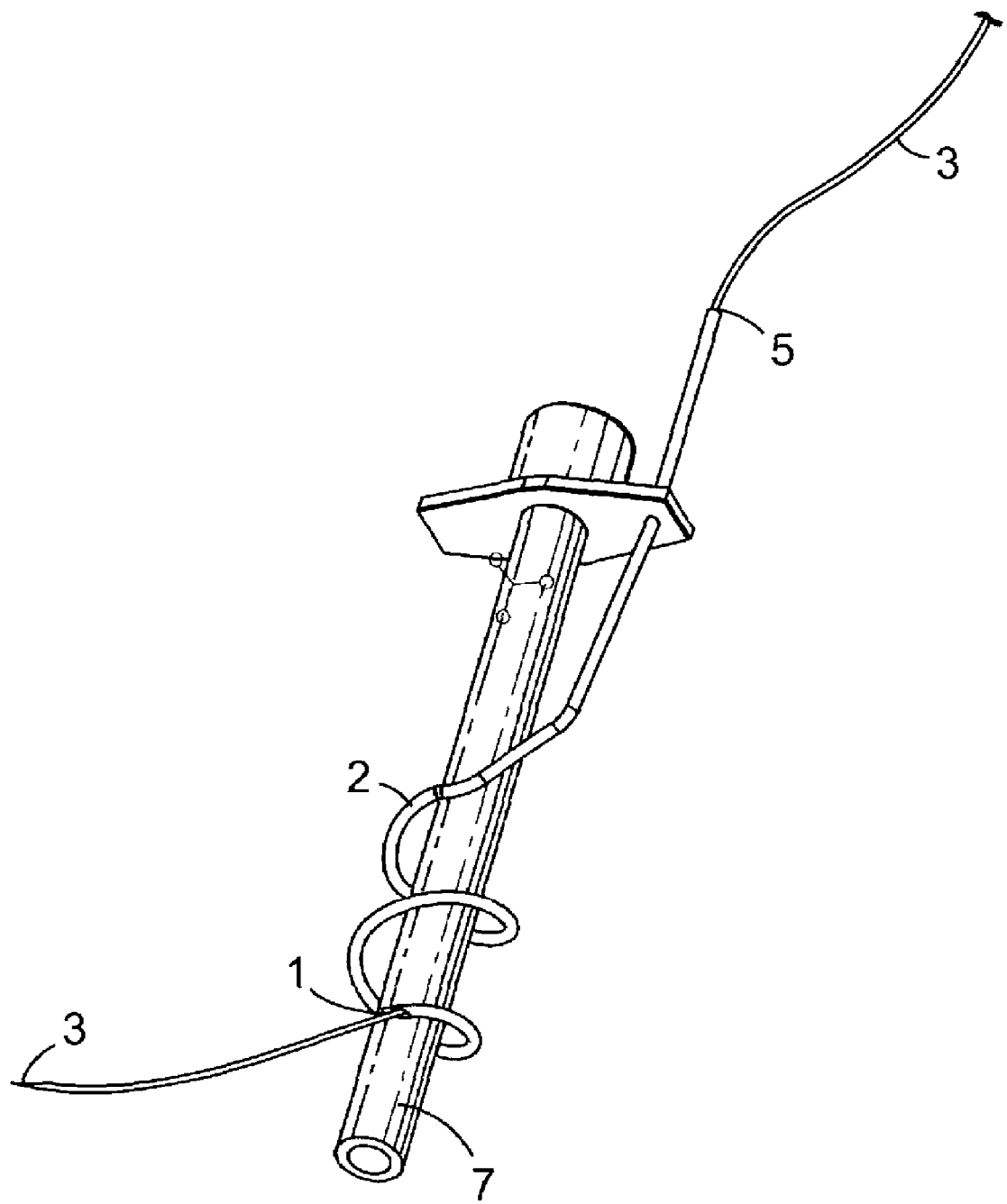
FIG. 5 is a perspective view of an embodiment of implantable member deployment element according to the present invention, showing a suture as the implantable member.

FIG. 5 illustrates another embodiment of an implantable article deployment member 2 according to the present invention. The transurethral deployment member comprises a substantially helically shaped hollow tube 2. The tube 2 has a tip 1 for penetrating the wall of the urethra. A suture 3 is threaded within the tube 2. Preferably, the tube 2 is constructed of a material that affords relative movement between the suture 3 and tube 2 so that the tube 2 and suture 3 may be separated with the suture 3 left in the body.

In a preferred embodiment, the helical suture delivery apparatus consists of a helically formed stainless steel hypodermic tube 2 terminating on one end with a sharps for penetration into tissue and a straight end for loading of a suture material 3 or preformed metallic coil.

In one embodiment, the leading end of the suture or coil 3 may incorporate a barb type anchoring piece for fixation of the suture or coil into the target tissue. Alternatively, the holder may comprise the non-sharp anchoring means disclosed in U.S. Pat. No. 6,382,214. In this embodiment, a feature responsible for separating the implantable article from the surgical instrument (the "separator") is part of the implantable article itself.

The helically formed hypo tube 2 is preferably mounted in a stabilizer piece (not shown) that aids in introduction of the device around the urethra and keeps the urethra straight while performing the procedure.

The stabilizer piece may optionally serve to accept a rigid scope for visualization during the procedure. Alternatively, other visualization means, such as ultrasound, may be optionally utilized for use with the present invention.

Figure 6:
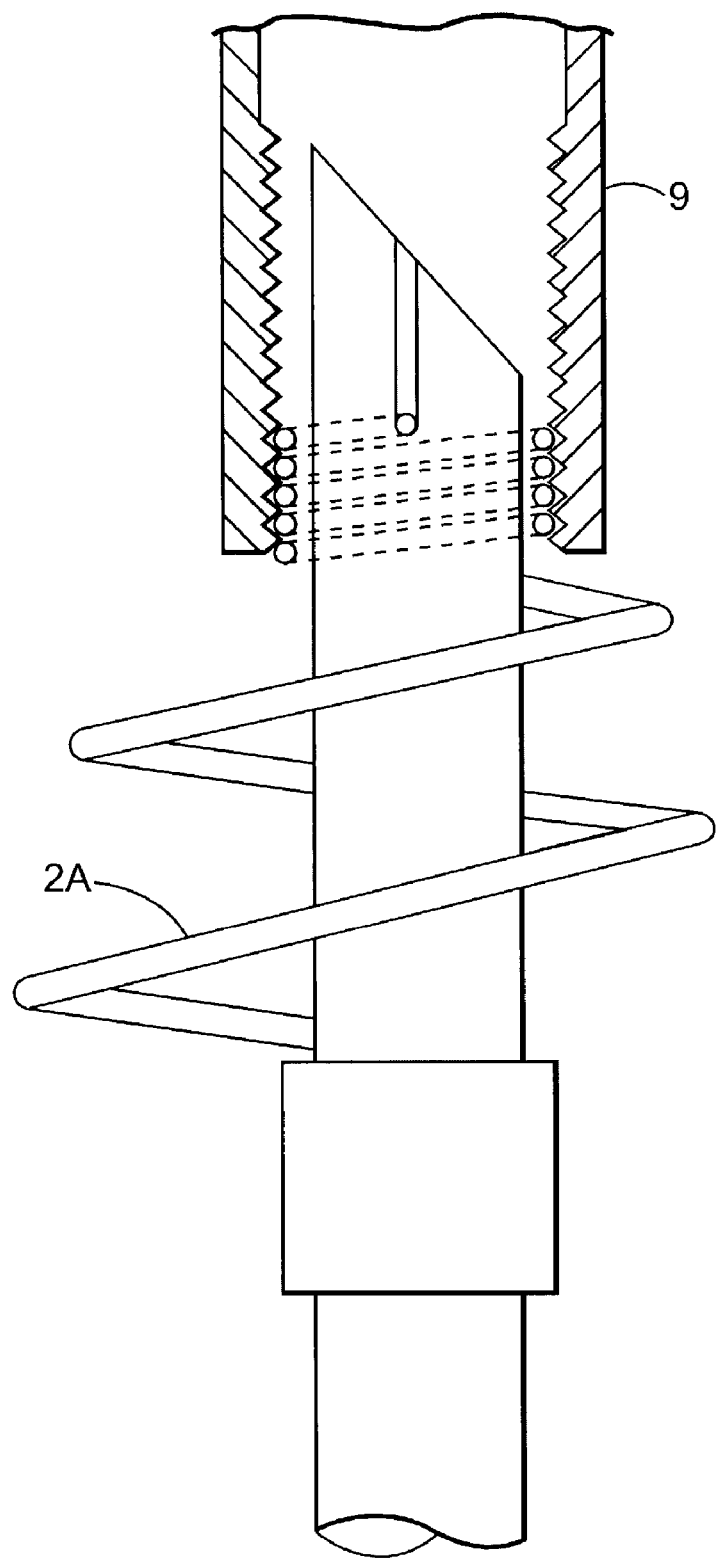
FIG. 6 is a side view of another embodiment of implantable member deployment element according to the present invention.

FIG. 6 illustrates an additional embodiment of the present invention wherein the implantable article deployment member and actuator for moving the deployment member include wrapping a conical implantable article (e.g. a spring) 2A around a rod, placing it in a tube 9, placing the tube in a proper anatomical position, and deploying the implantable article 2A out the open end of the tube 9.

Adding a thread to the deployment rod 9 adds advantages in both loading and deploying. One advantage is that it makes it easier to wrap the spring 2A around the rod as the threads will provide a track for the implantable article 2A to lie in. This will prevent the spring 2A from moving on the rod as it is inserted into the deployment sheath as well as help to keep it tightly compressed. Also, keeping the spring 2A tightly wound and compressed will also help minimize the distance the deployment rod has to be extended into the body cavity to deploy the spring 2A. It will also keep the spring from binding in the outer sheath allowing the spring to be pushed out from behind rather than pulled out by the top of the spring. By keeping it tightly wound on the deployment rod, the threads will prevent the spring 2A from being stretched out as it is dragged through the deployment tube, preventing deformation of the spring 2A. The threads will also prevent the coils of the wound spring 2A from crossing over one another and thus changing the way the spring functions once deployed. It is also believed to prevent the spring 2A from seizing up inside the tool as it is advanced along the outer sheath.

Figure 9:
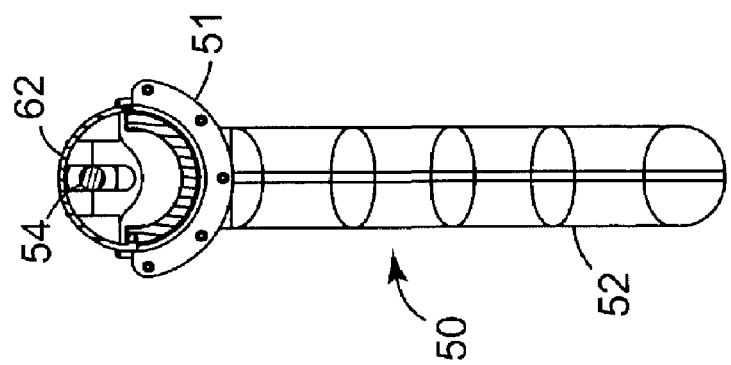
FIG. 9 is a sectional view of the surgical instrument of FIG. 8 taken approximately along lines 9—9 of FIG. 8.
Figure 8:
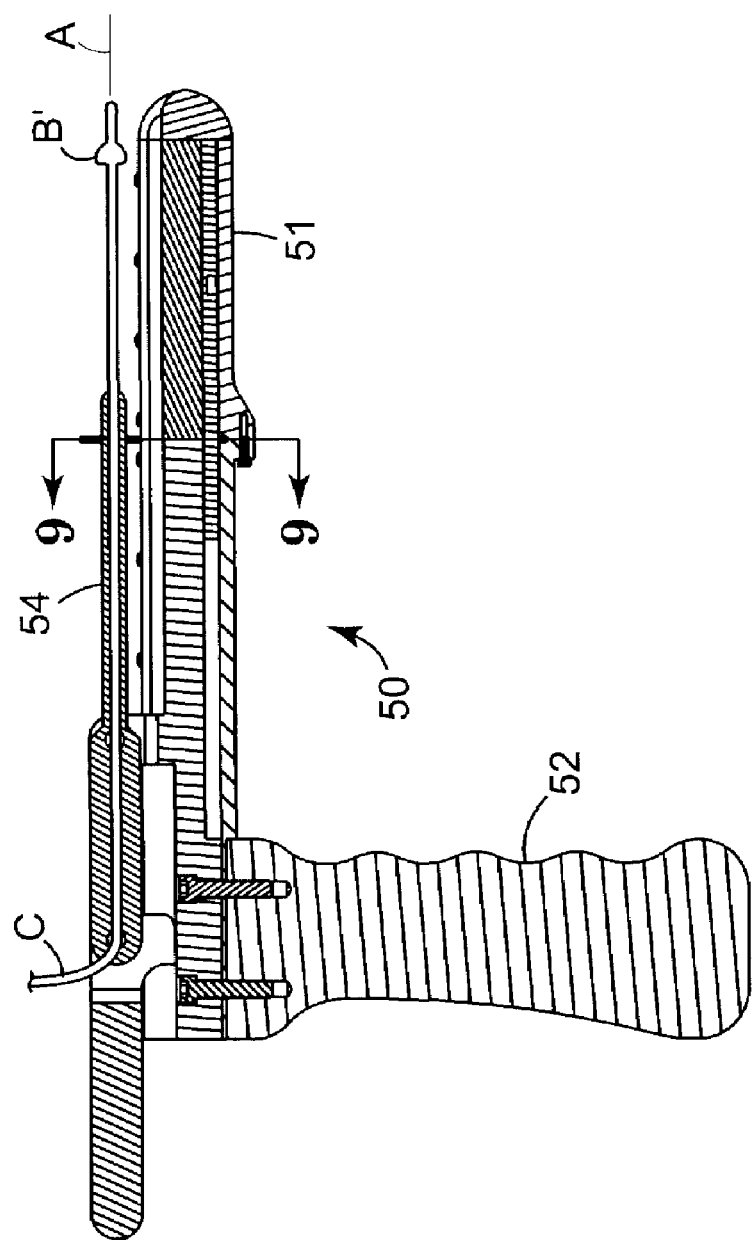
FIG. 8 is a side view of another embodiment of surgical instrument according to the present invention.

Referring now to FIGS. 8 and 9, there is shown another embodiment of surgical instrument 50 according to the present invention. The surgical instrument 50 is capable of implanting an implantable article without piercing or traversing the wall of the tubular tissue structure (e.g. the urethra).

The surgical instrument 50 includes a handle 52, and an elongate urethral immobilizer 54 that is sized and shaped to be placed within the urethra. The surgical instrument also includes an implantable article deployment member 62 that capable of moving along a path that is entirely external to the urethra.

A portion 51 is sized and shaped to be inserted into the patient's vagina so that the implantable article deployment member 62 may be positioned mid-urethra. Additional incisions or dissection may be utilized to optimize access to the urethra, according to surgeon preference. For example, a surgeon may decide to make two small (e.g. one inch long) incisions in the vagina, one approximately at the mid urethra and one approximately at the bladder neck in order to afford a desired access to the urethra.

The surgical instrument 50 optionally includes an inflatable member B' for positioning the instrument 50 relative to the tubular tissue structure. A catheter C may be utilized for this purpose. For example, the balloon B' and neck thereof may be placed to place the implantable article deployment member 62 mid urethra.

Figure 7:
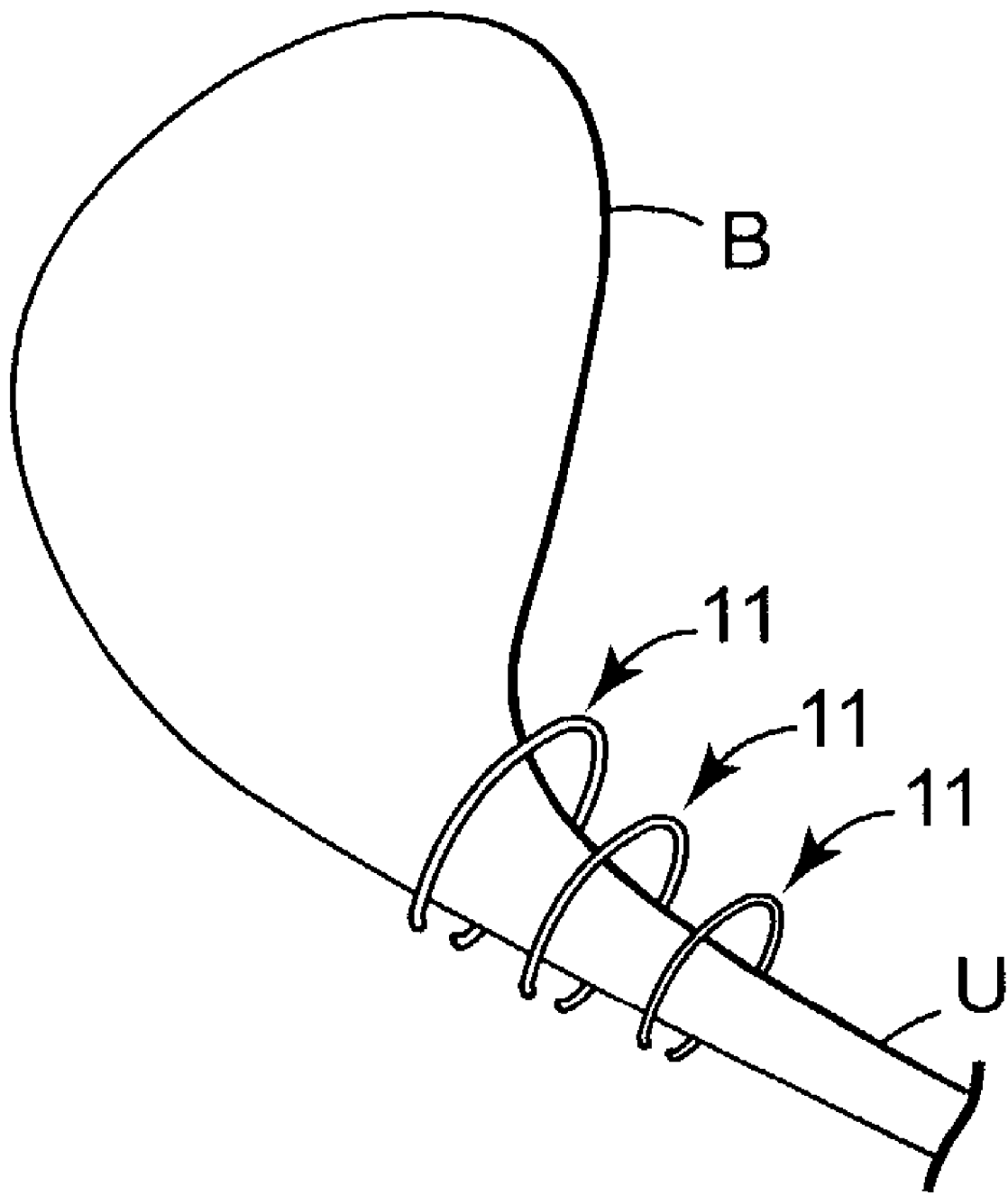
FIG. 7 is a schematic depiction of another embodiment of the present invention with a plurality of discrete implantable members deployed in a non-helical (semi-circular) fashion about the urethra.

Notably, the implantable article need not be helical in shape. FIG. 7 illustrates a plurality of discrete semi-circular or horseshoe shaped implantable articles 11. Alternatively, when the implantable articles comprise sutures, the implantable articles may comprise substantially circular implants, e.g. tied by a surgeon via access through a vaginal incision. Optionally, the sutures may be tied in an adjustable knot (e.g. a slip knot or any of the adjustable knots disclosed in U.S. patent application Ser. No. 10/004,185 filed Oct. 30, 2001) so that the tension on the knots may be adjusted post or perioperatively.

Figure 10:
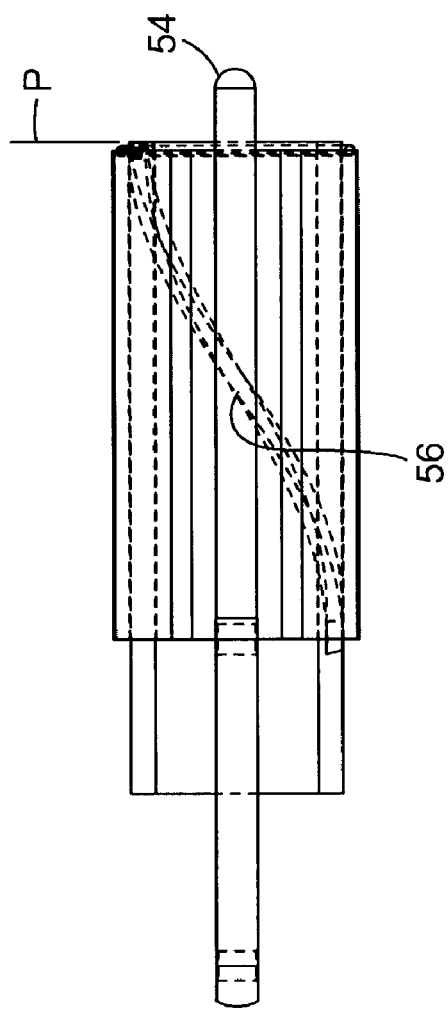
FIG. 10 is a top view of a portion of an actuator which may be used with the surgical instrument of FIG. 8, showing an internal cam track in dashed lines.
Figure 11:
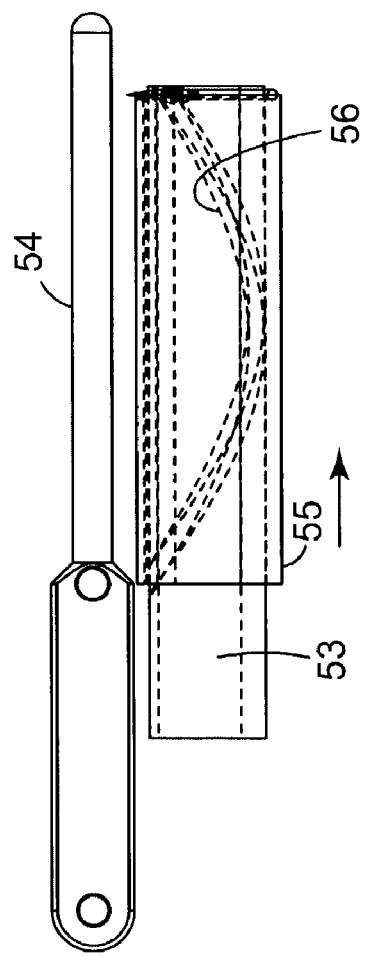
FIG. 11 is a side view of the components of FIG. 10.
Figure 16A:
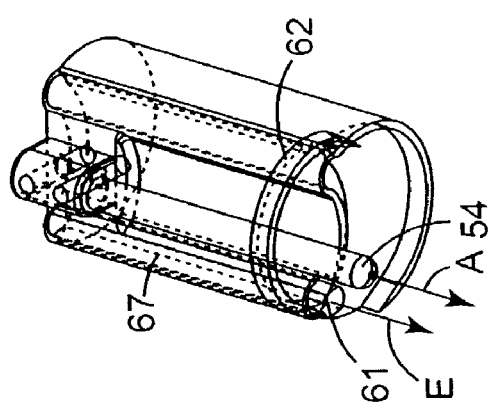
FIG. 16*a* is a perspective view of the implantable member deployment element in an extended position.
Figure 16B:
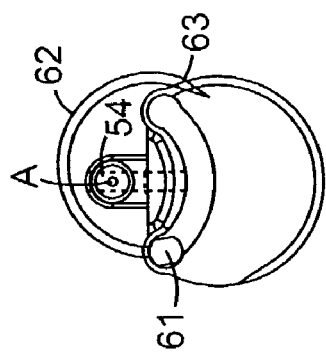
Figure 15A:
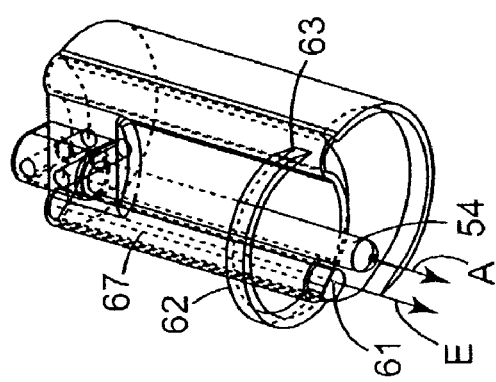
FIG. 15*a* is a perspective view of the implantable member deployment element more fully extended than in FIG. 14*a*.
Figure 15B:
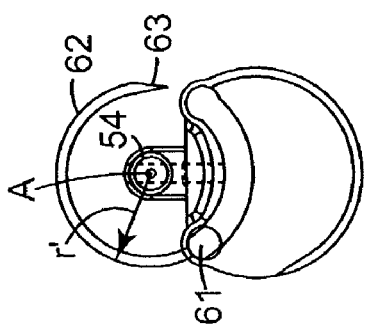
FIG. 15*b* is an end view of the components of FIG. 15*a*.
Figure 14A:
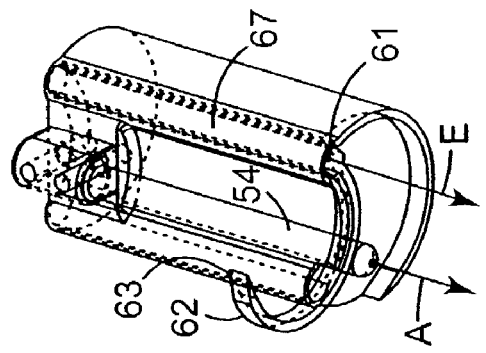
FIG. 14*a* is a perspective view of the surgical instrument with an implantable member deployment element partially deployed about a tubular tissue immobilizer.
Figure 14B:
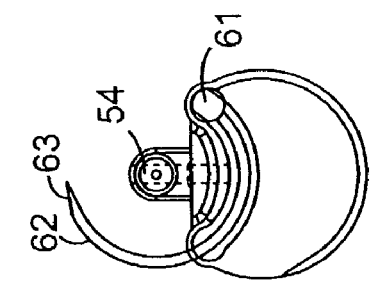
FIG. 14*b* is an end view of the components of FIG. 14*a*.
Figure 13A:
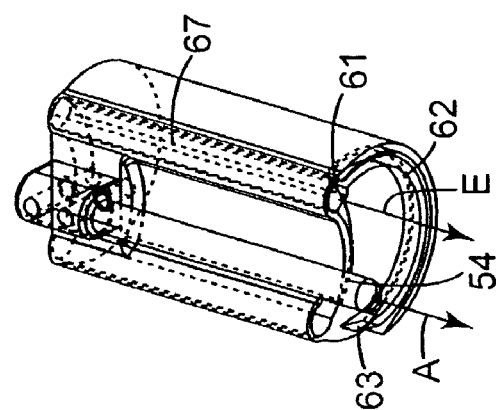
Figure 13B:
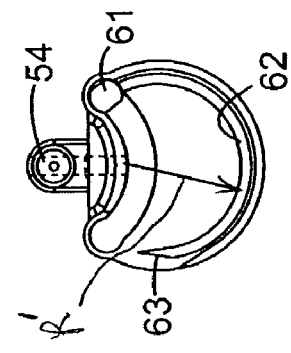
FIG. 13*b* is an end view of the components of FIG. 13*a*.

Referring to FIGS. 9 through 11, there is shown an actuator for moving an implantable article deployment member (e.g. 62 for the instrument of FIGS. 8 and 9) between the retracted and extended positions. The actuator comprises a slidable guide member with a helical cam groove and a cam follower associated with the implantable article deployment member 62.

Figure 12:
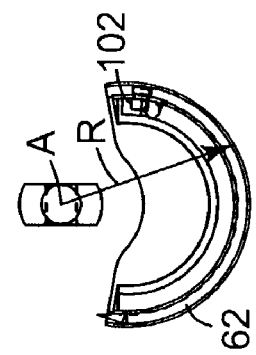
FIG. 12 is an end view of a portion of the components of FIG. 10.

In general, the cam 55 drives the cam follower 102 (see FIG. 12). As the cam is driven forward (see the arrow in FIG. 11), the cam follower is driven in a circular motion. FIG. 10 shows the deployment member's 62 plane of motion P. The arcuate end portion of the deployment member 62 (see FIG. 12) is restricted to this plane. In a preferred embodiment, the cam follower 102/deployment member 62 may be restricted in motion to the plane P and about a single axis.

FIGS. 13*a* through 16*b* sequentially illustrate one option for the effect of an actuator for moving the implantable article deployment member 62 between the retracted and extended positions. The immobilizer 54 has an axis A and the path of the implantable article deployment member 62 is substantially semi-circular about the axis A. The implantable article deployment member 62 preferably includes a semi-circular portion having a radius R' (FIG. 13*b*) approximately the radius r' of the path about the axis A of the immobilizer 54 (FIG. 15*b*), but slightly less. The semi-circular portion has a leading end 63 and a trailing end 61. The implantable article deployment member 62 also has an elongate member 67 projecting substantially perpendicular to the semi-circular portion from the trailing end 61. The elongate member 67 has an axis E.

The actuator for rotating the deployment member between the retracted toward the extended position is preferably a mechanical linkage comprised of a series of gears for affording rotation about two distinct axes.

Referring now to FIGS. 20 through 23, there is shown an embodiment of actuator that includes, in part, a mechanism for converting rotational motion to linear motion. The actuator comprises gears, detents and grooves. As described below, the mechanical linkage actuator includes male and female splines, cams and cam followers.

An activatable (e.g. rotatable) handle or knob (e.g. see 95, FIG. 19) is adapted to actuate deployment member 92 and is associated with a pinion gear 109. Returning to FIGS. 20 through 23, a female spline gear (inside 109, so not shown) is associated with the internal diameter of the pinion gear 109. As the pinion gear is rotated the female spline gear is rotated a predetermined amount (e.g. equal). Mated to the female spline gear is a male spline gear. As the female spline gear rotates, the male spline moves linearly. The male spline is associated with a cam such that as the male spline gear moves linearly, the cam moves as well. A cam follower 102 is attached to the deployment member 92 and follows cam groove 105.

The first rotation depicted in FIGS. 13*b* to 14*b* may be accomplished by rotating the actuating knob 95. This rotates the pinion gear and in turn rotates the female spline gear. Rotation of the female spline gear advances the male spline, thereby advancing the cam. As the cam is advanced the deployment member 92 is rotated from the position in FIG. 13*b* to the position in FIG. 14*b*. This rotation is about axis E. This action occurs since the pinion gear 109 is attached to the knob 95 that is used to drive the assembly. All motion goes through the pinion gear. In one embodiment, the pinion gear only has 5 teeth.

For this first rotation, the pinion gear may be turned (e.g. approximately 180 degrees) which drives the female spline (which rotates approximately 180 degrees) which drives (linearly) the spline (male) forward. The cam is fixed to the male spline as the male spline moves forward, the cam moves forward and drives the cam follower that is attached to the needle pin, through the first rotation (e.g. about 100 degrees, compare FIGS. 13*b* and 14*b*).

With continued rotation of knob 95, a second rotation occurs when the pinion gear makes contact with the rack gear 107 and is made to follow about the rack 107 for about seventy degrees. Preferably, the rack gear 107 is centered about axis A. Note this rotation is about a secondary axis (compare FIGS. 14*b* and 15*b*). Rotation of the pinion gear about the rack gear advances the deployment member from the position of FIG. 14*b* to that of FIG. 15*b*. This rotation is about axis A, not axis E. Notably, the shape of the groove 105 can include a flat or other shape to compensate for the rotation caused by rack gear 107.

The third rotation occurs after the pinion gear releases or disengages from the rack gear and turns freely again. Continued rotation advances the male spline forward, driving the cam forward and thus advancing the deployment member further. The pinion gear moves through a third rotation of about 100 degrees and drives the female spline accordingly which drives the male spline forward, which in turn drives the cam forward, which drives the cam follower through the third rotation of about 50 degrees. This rotation is depicted in the change between FIGS. 15*b* and 16*b*. The axis of rotation is again about E.

Figure 18:
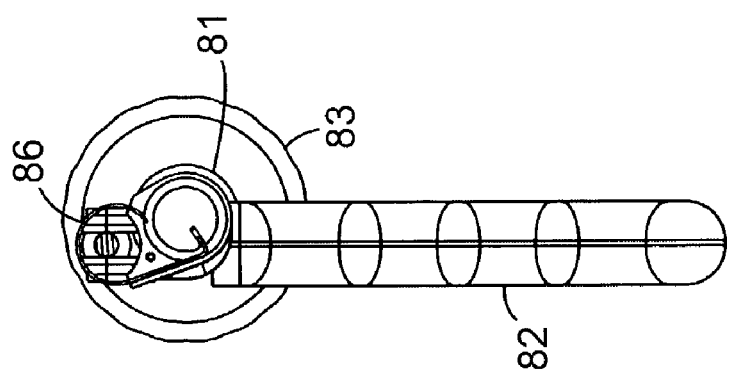
FIG. 18 is a sectional view of the surgical instrument of FIG. 17 taken approximately along lines 18—18 of FIG. 17.
Figure 17:
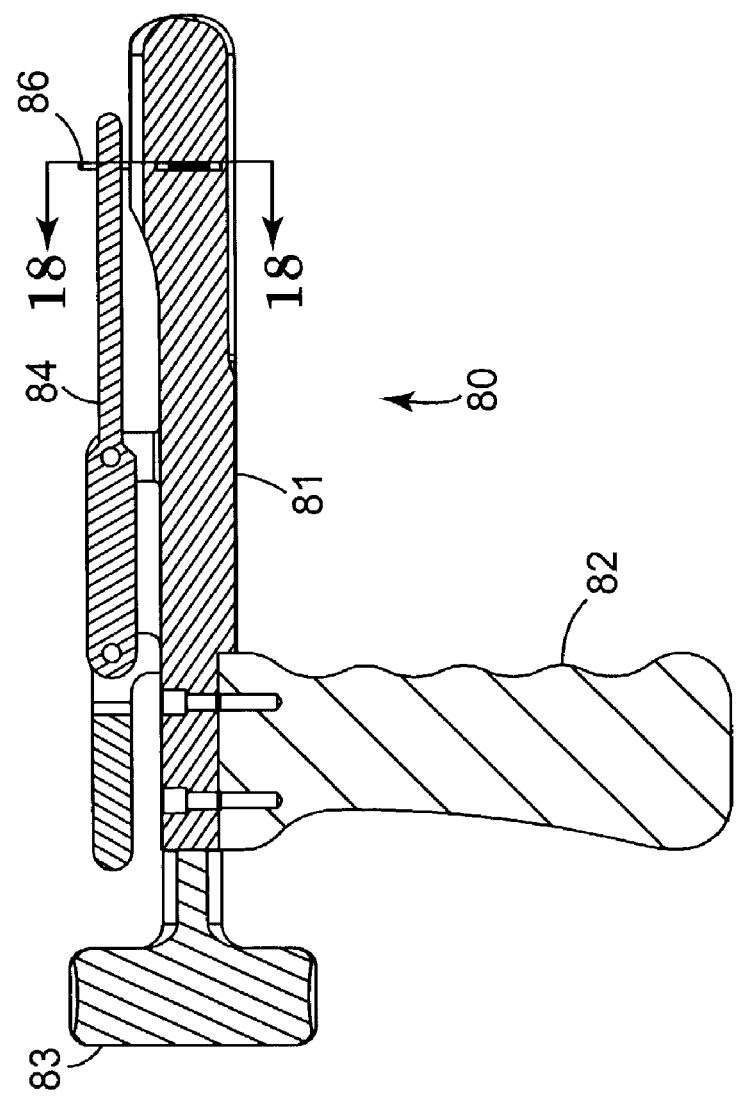
FIG. 17 is a side view of another embodiment of surgical instrument according to the present invention.
Figure 18A:
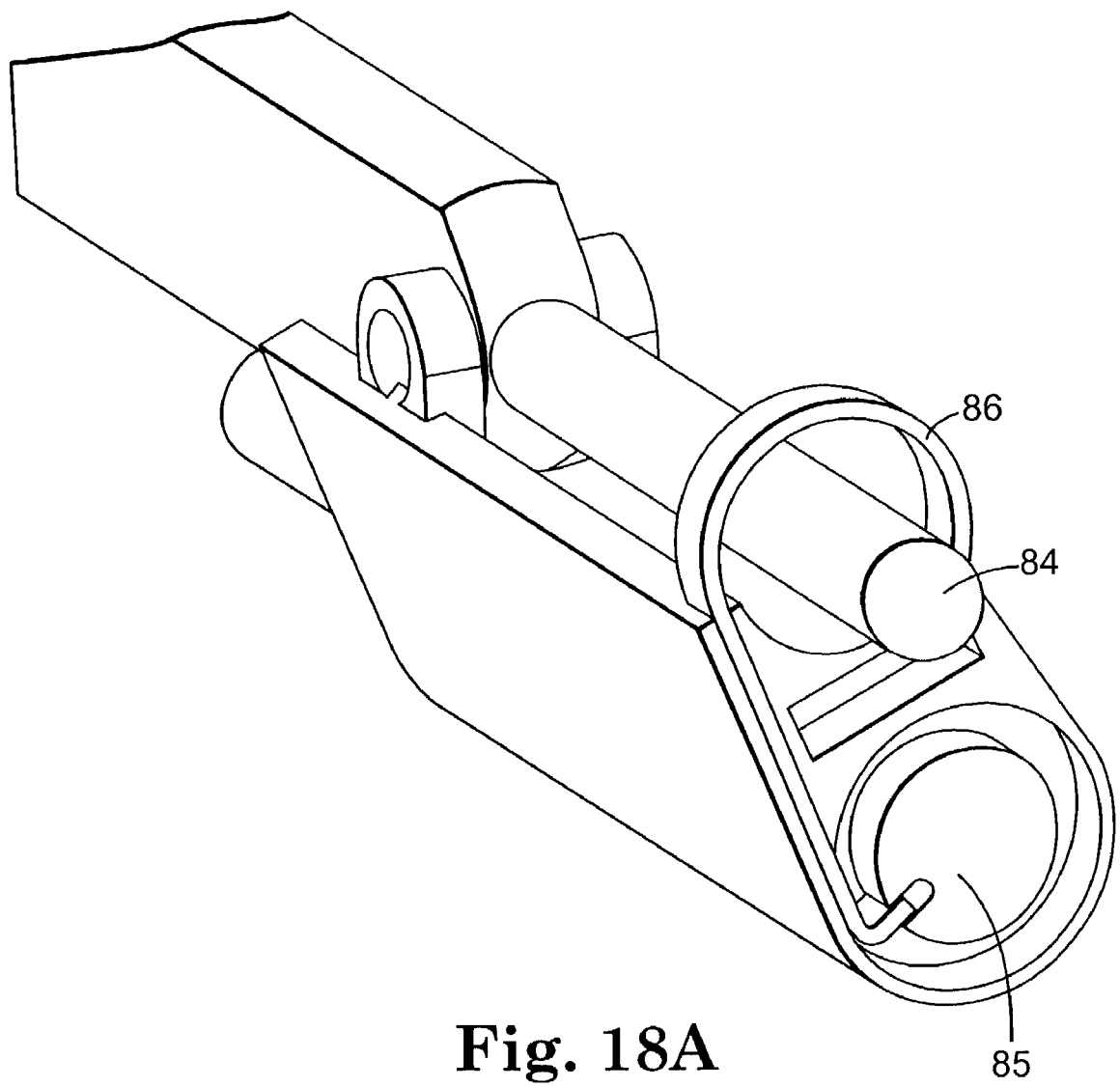
FIG. 18A is a schematic perspective view of portions of the embodiment of FIGS. 17 and 18.

Referring now to FIGS. 17–18A, there is shown another embodiment of surgical instrument 80 according to the present invention. The instrument 80 includes a urethral immobilizer 84, implantable article deployment member 86, a handle 82 and a portion 81 adapted to be inserted in the vagina. As best seen in FIG. 18A, the means for moving the implantable article deployment member 86 between the retracted and extended positions comprises a rotatable member 85 that is manually actuated by rotatable knob 83 (FIG. 17).

The implantable article deployment member 86 is composed of a shape memory material capable of resiliently deflecting into a predetermined shape during movement from the retracted toward the extended position. Suitable materials include nitinol, spring steel, or certain grades of stainless steel, and combinations of such materials and polymeric materials. As best seen in FIG. 18A, the leading end of the deployment member 86 includes a substantially linear shape in the retracted position but resiliently deflects to a semicircular shape as the deployment member emerges from the surgical instrument 80 and moves to the extended position.

Figure 19:
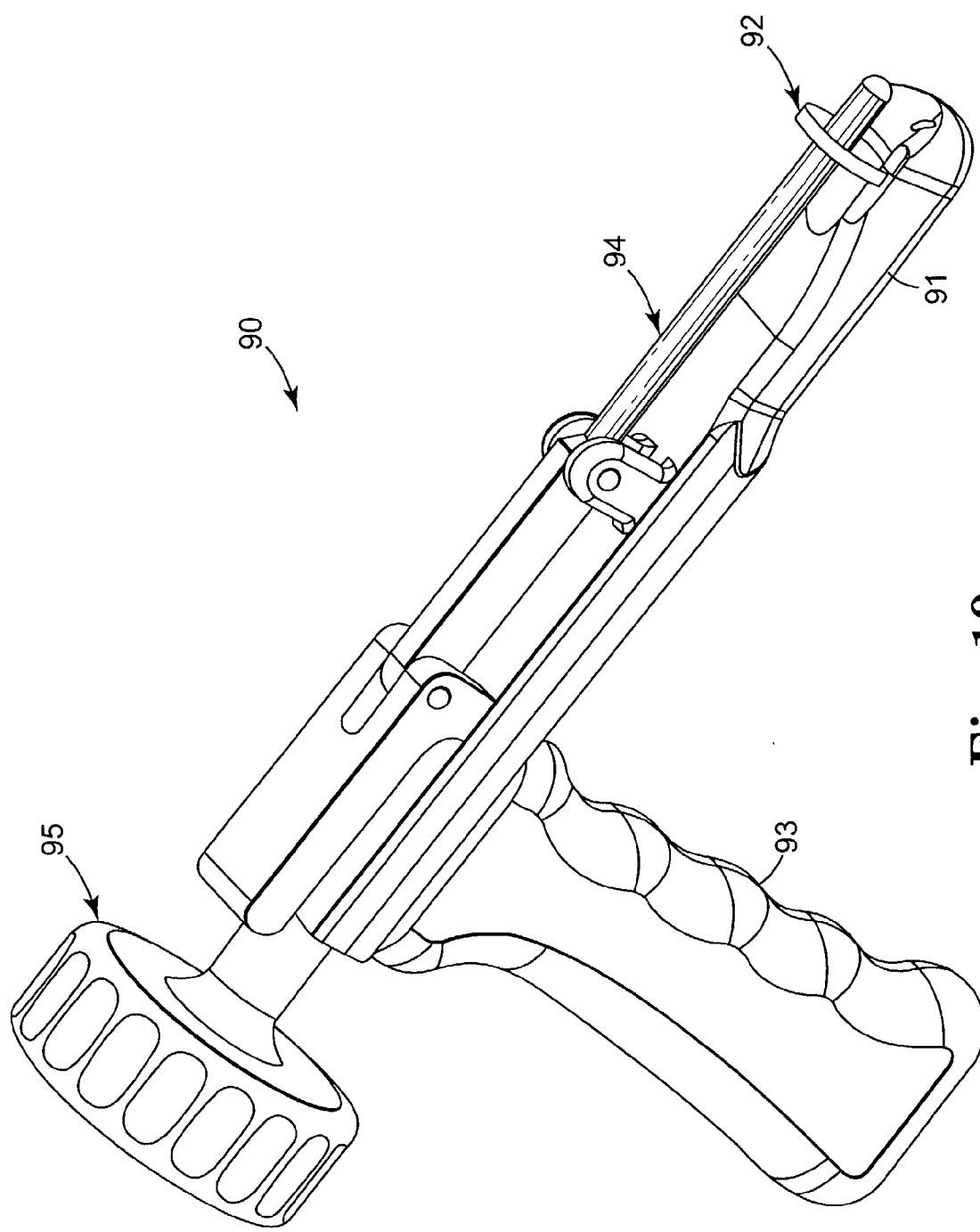
FIG. 19 is a perspective view of another embodiment of surgical instrument according to the present invention.
Figure 20:
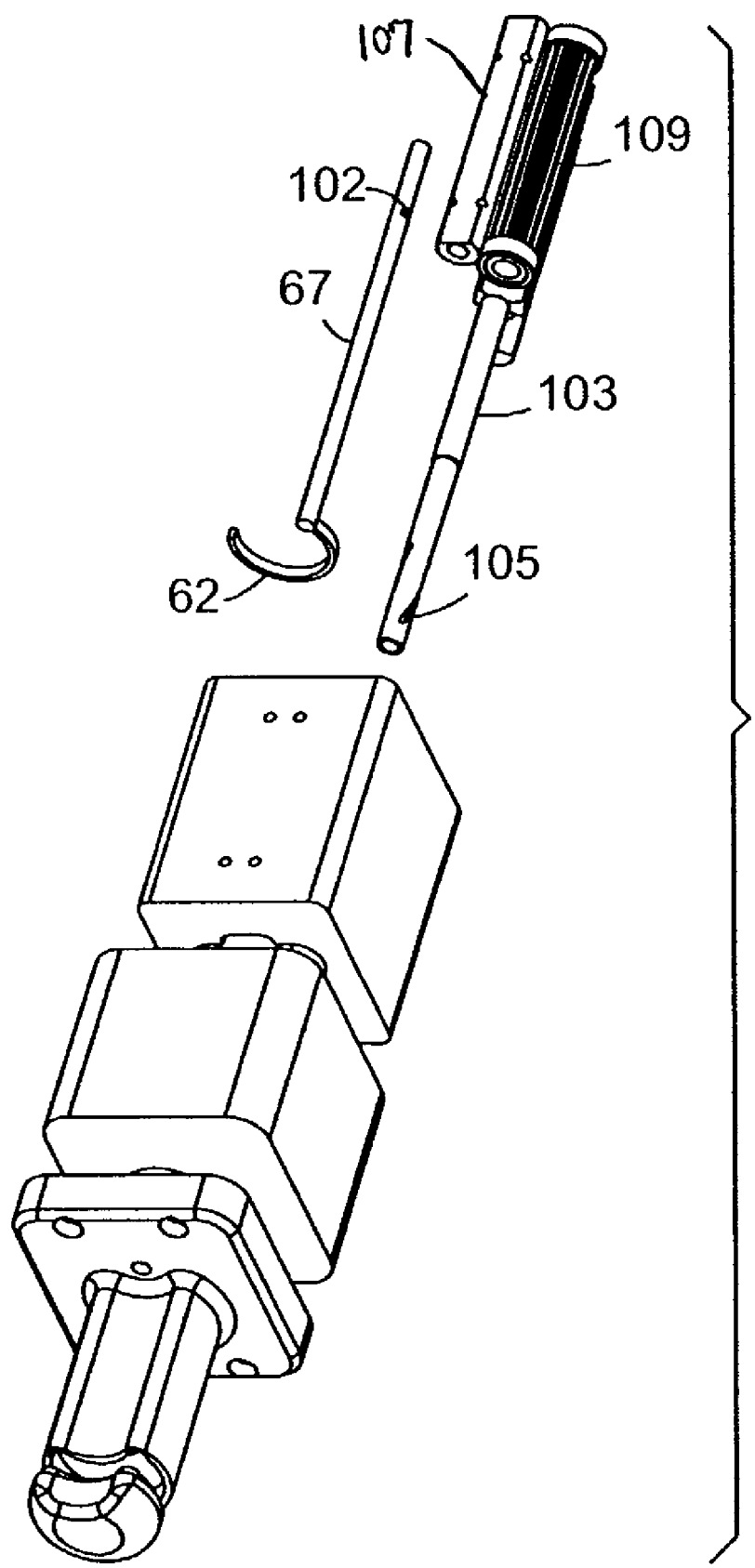
FIG. 20 is an exploded perspective view of components of an actuator for an implantable article deployment member for surgical instruments according to the present invention.
Figure 21:
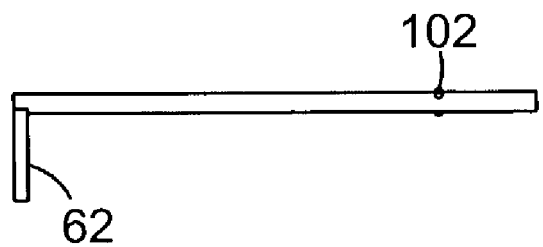
FIG. 21 is a side view of an implantable member carrier of FIG. 20 with a guide detent or cam follower.
Figure 22:
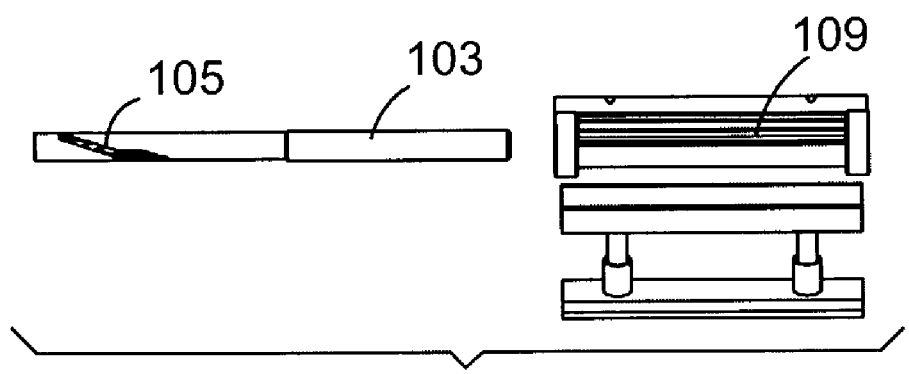
FIG. 22 is a side view of components of FIG. 20 including a guide member with a groove capable of engaging the detent shown in FIG. 21.
Figure 23:
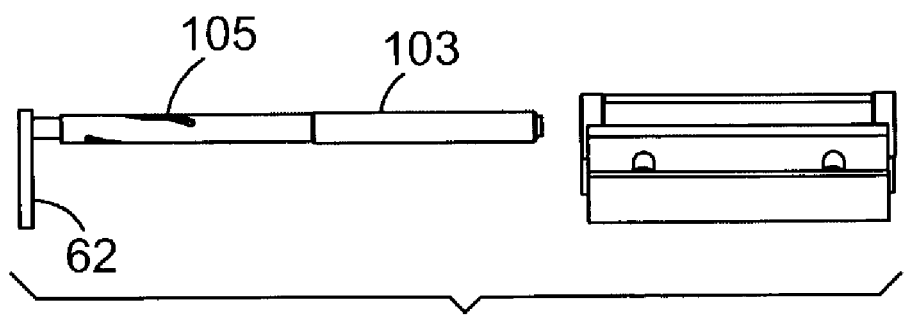
FIG. 23 is a side view of components of FIG. 20 with the implantable member carrier and guide member partially assembled.

FIG. 19 discloses another embodiment of surgical instrument 90 according to the present invention. The instrument includes a handle 93, a portion 91 for placement in the vagina, an implantable article deployment member 92, and a urethral stabilizing pin 94. This embodiment shows an manually activated (via knob 15) actuator and is free of any balloon or catheter.

The surgical instruments according to the present invention also include a capturing means or holder for retaining the implantable article in the patient's body once the implantable article deployment member (e.g. 62) moves to the extended position and then back toward the retracted position. Preferably, the surgical instruments include a separation means for separating the implantable article from the surgical instrument. These features are described more fully below.

Figure 24:
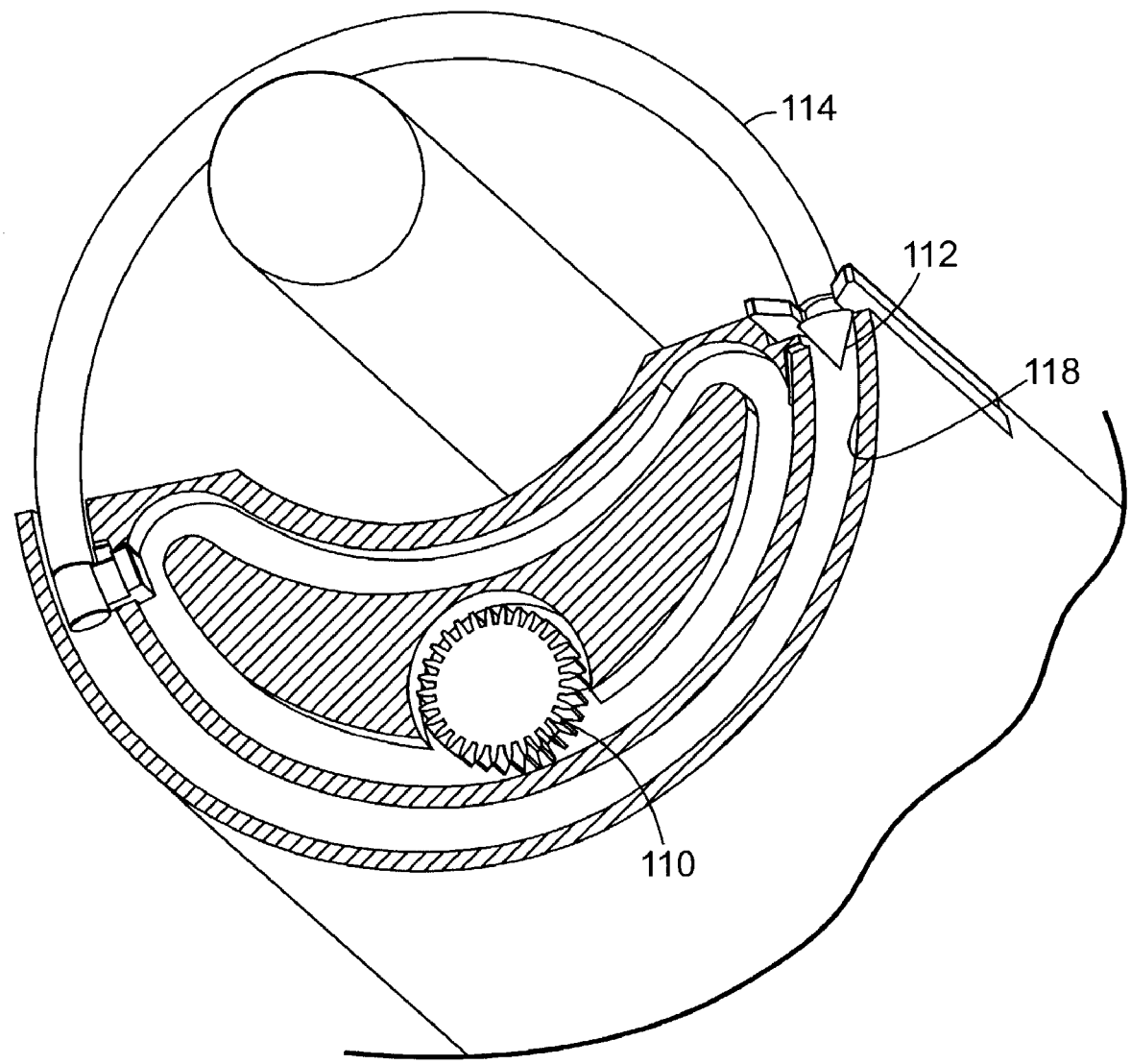
FIG. 24 is a perspective, end view of another embodiment of surgical instrument according to the present invention.
Figure 25:
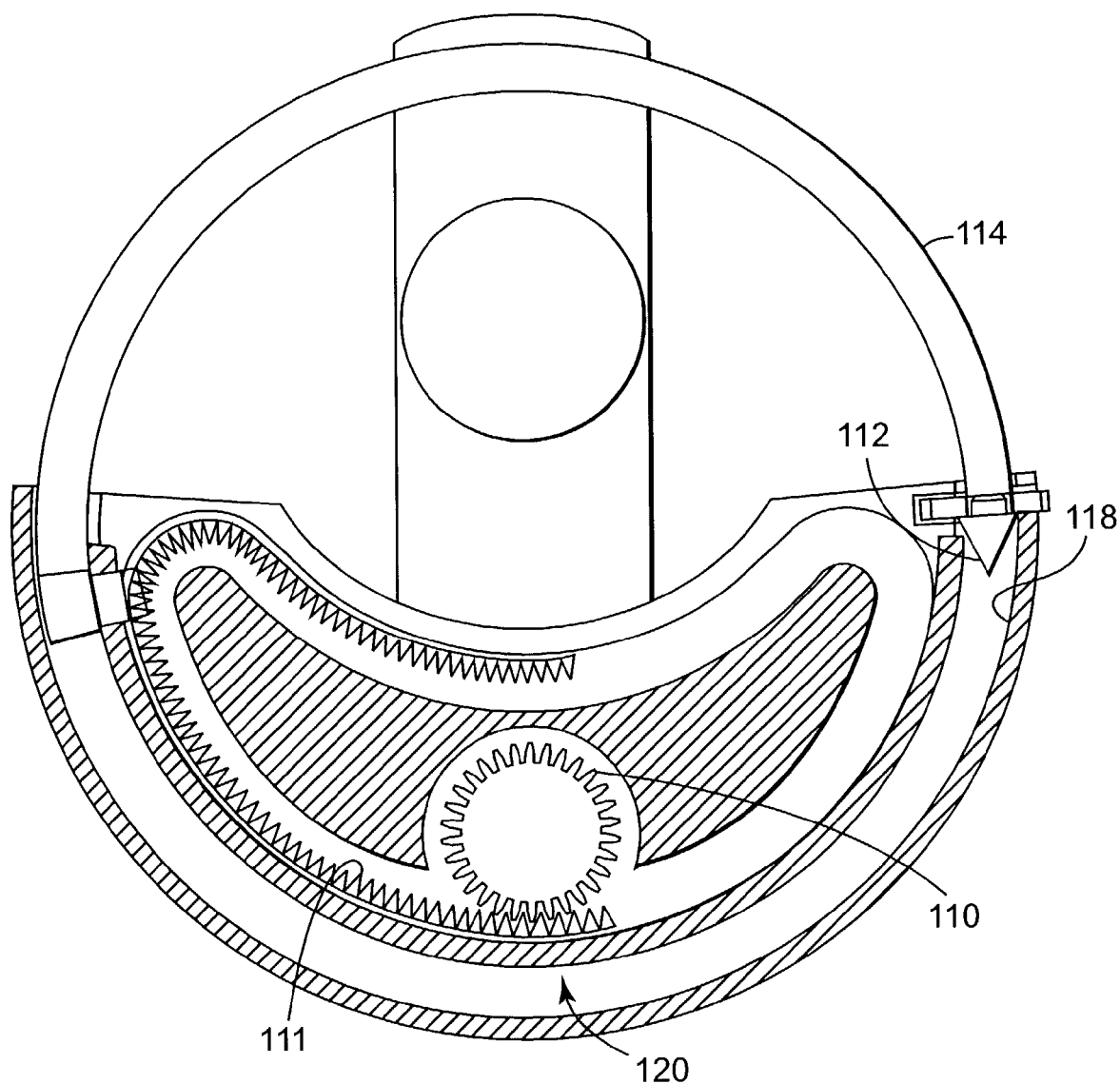
FIG. 25 is an end view of another embodiment of surgical instrument showing a gear and gear track.

FIGS. 24 and 25 show an embodiment wherein the actuator for moving the implantable article deployment member 114 between the retracted and extended positions comprises a gear 110 and a predetermined shaped gear track 111. In this embodiment, the implantable article comprises a suture having a dart associated with a leading end thereof or a "suture and dart assembly".

The suture and dart assembly can comprise any suitable assembly. As used herein, the term "suture and dart assembly" is used broadly to include any suture and any structure that affords passage of a suture through tissue. For example, the dart may comprise a substantially right circular cone shaped dart with a sharp tip and a base surface. The dart may be constructed from stainless steel (e.g. 17-4 PH 630 SST) and include a neck portion capable of being crimped or swaged to an end of a suture. The cone may have an included angle of about 41 degrees, a base diameter of about 0.075 inches. The overall length of the dart may be about 0.17 inches and the length of the cone may be about 0.1 inches.

Figure 26:
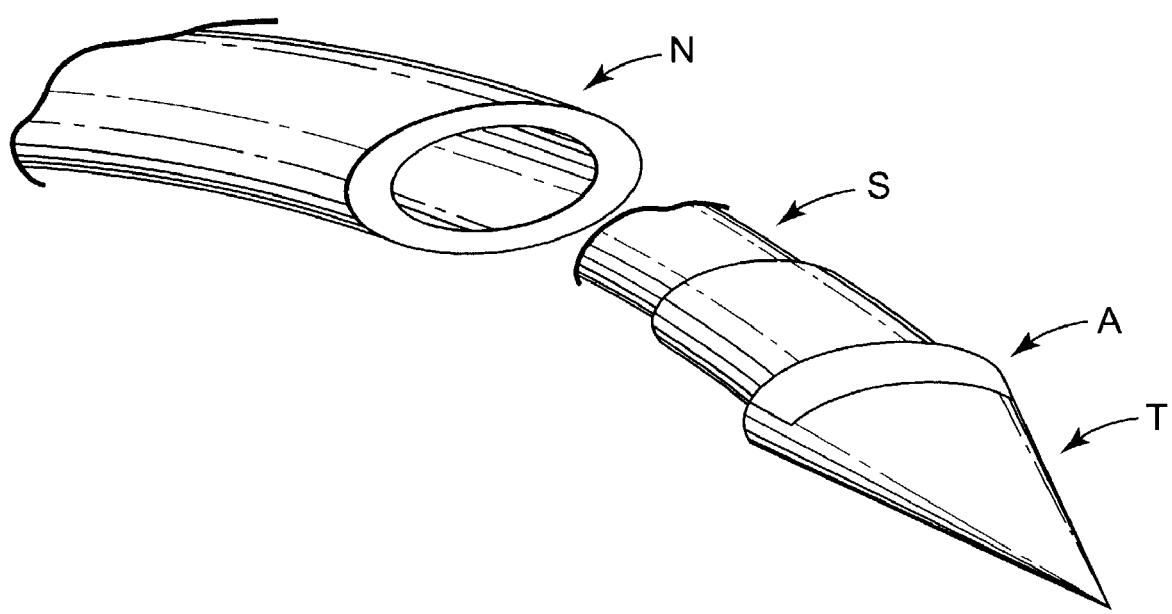
FIG. 26 is a perspective view of an implantable member deployment element, an implantable member in the form of a suture, and a leading element of the suture according to one aspect of the present invention.

FIG. 26 shows another example of suture and dart assembly. The suture S has a leading element T that is suitable for passing through tissue and that has a shoulder surface A for engaging drive surfaces on implantable article deployment member N.

As another example, not intended to be limiting, the dart of the assembly can include trocar-like sharp cutting surfaces that intersect at a sharp tip. A commercial example of such assembly includes a Capio Braided Polyester 0 Suture with tapercut, available from Boston Scientific Corp. of Watertown, Mass. Suitable materials for the dart include, for example, titanium and stainless steel.

The surgical instruments of the present invention include a holder for leaving the implantable article in the patient once the implantable article deployment member moves to the extended position. As seen in FIGS. 24 and 25, the holder may comprise a clip for engaging a trailing end of the dart. The clip holds the suture and dart assembly in the deployed position when deployment member 114 moves back to the retracted position. The suture may be pre-cut so that the trailing end of the suture is revealed once the deployment member 114 is retracted or an internal cutter may be utilized to cut the suture. Alternatively, the surgeon may cut the trailing end of the suture. Alternatively, the surgical instruments according to the present invention may incorporate the suture passing assemblies and the suture and dart assembly capturing mechanisms disclosed in U.S. patent application Ser. No. 10/155,710 filed May 24, 2002, entitled, "Surgical Suture Passers and Methods."

Figure 27:
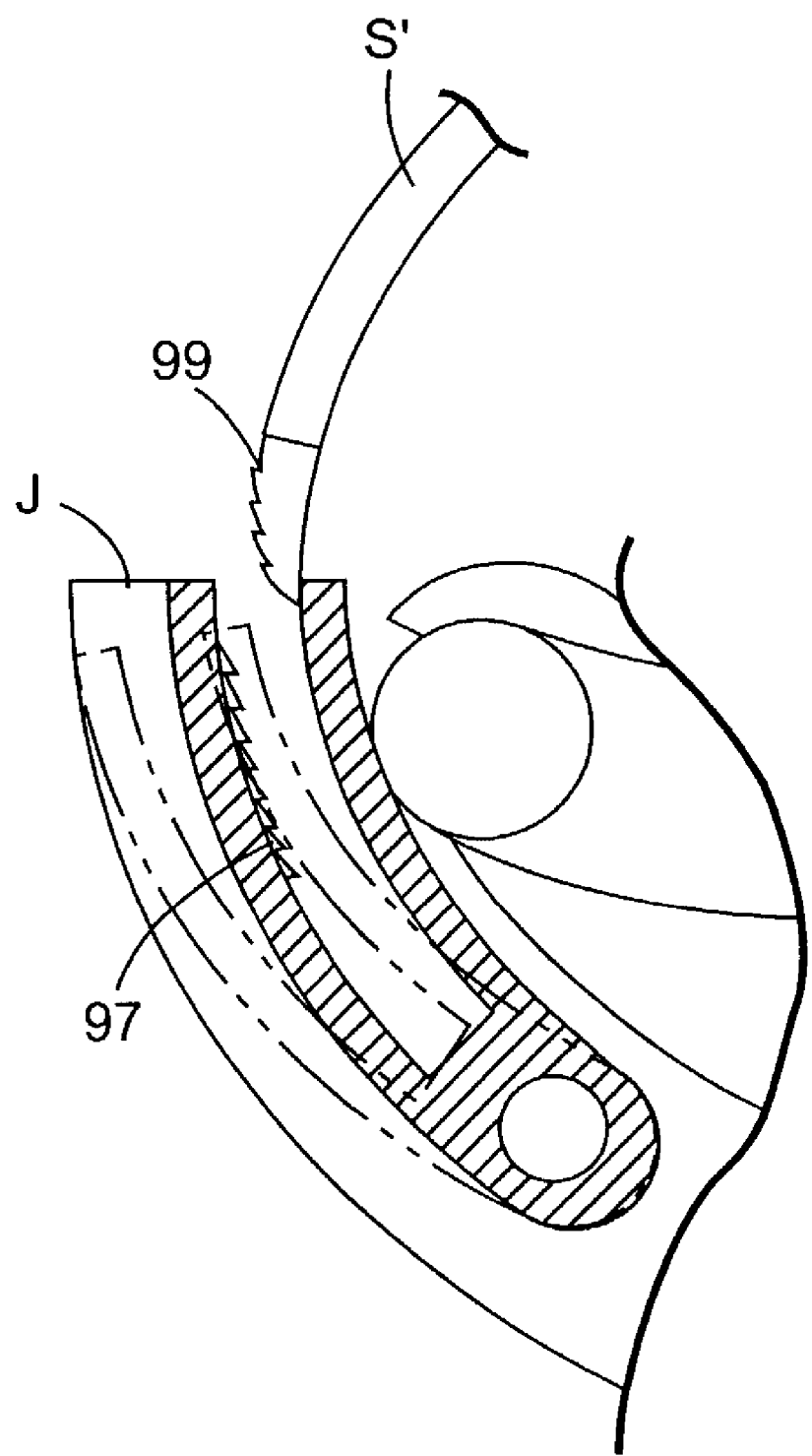
FIG. 27 is a schematic view of an embodiment of implantable member capturing mechanism according to the present invention.

FIG. 27 shows another embodiment of holder according to the present invention. The holder comprises specially shaped surfaces 97 in a jaw J of the surgical instrument. The suture S' includes a leading end with specially shaped surfaces 99 that complement the surfaces 97. Engagement between the surfaces 97 and 99 afford movement of the suture into the jaw but resist movement of the leading end of the suture S' out of the jaw J.

Figure 28:
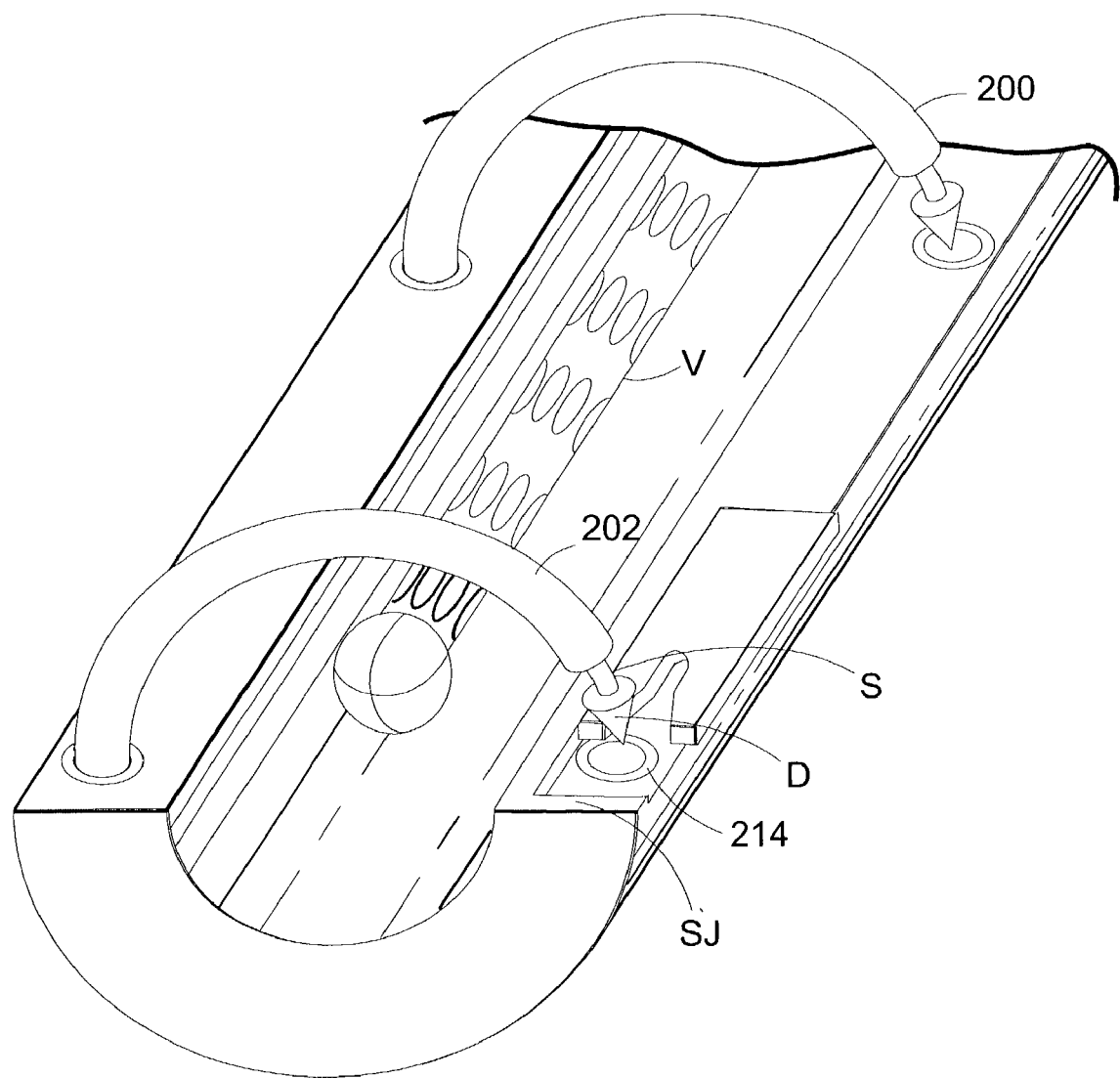
FIG. 28 is a perspective view of another embodiment of surgical instrument according to the present invention showing a plurality of discrete implantable member deployment elements.

FIG. 28 illustrates a surgical instrument for implanting a plurality of sutures S having a dart D associated therewith. The instrument includes a plurality of implantable article deployment members 200 and 202, a vacuum element V, and a dart capturing clip (optionally movable) on stationary jaw SJ.

Figure 29:
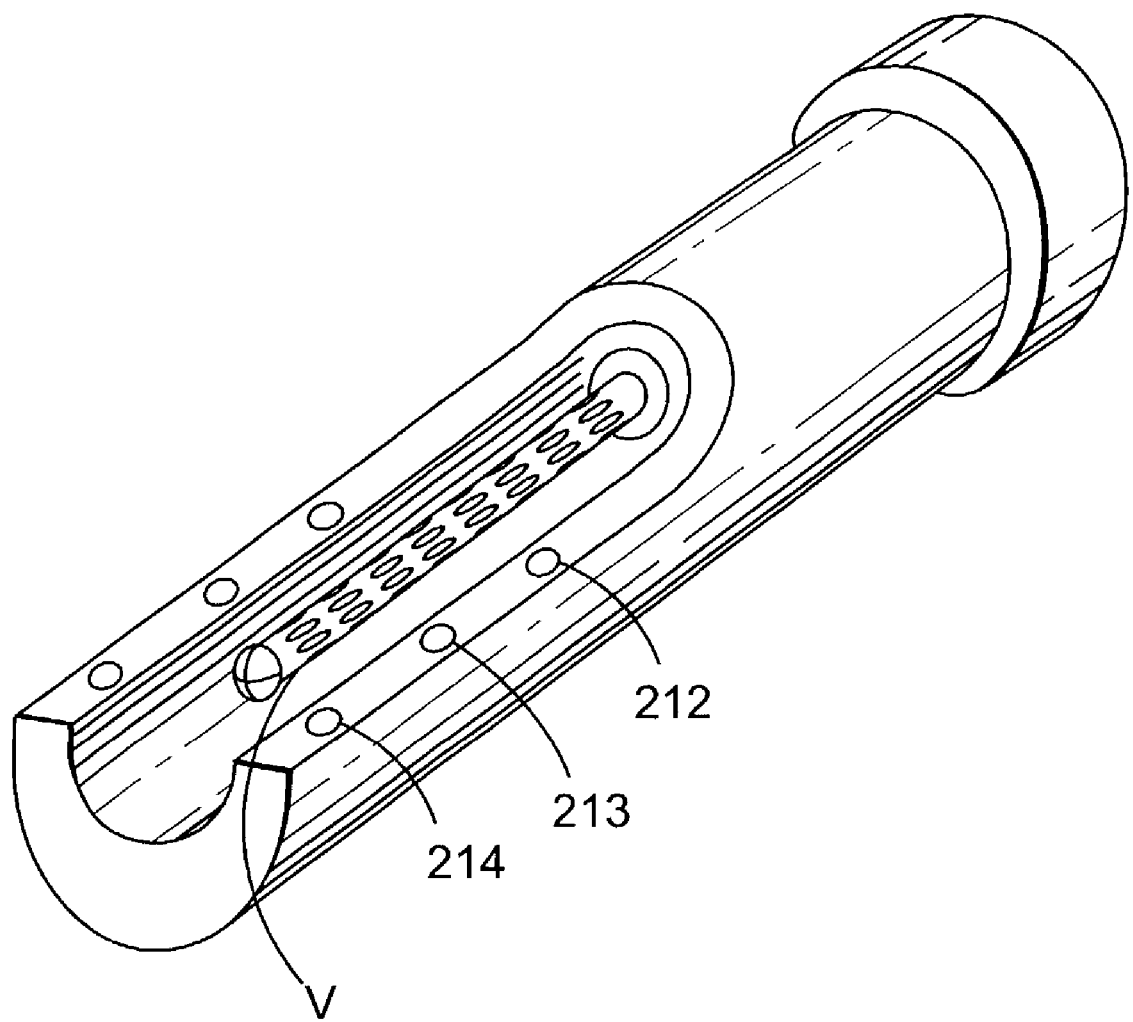
FIG. 29 is a perspective view of another embodiment of surgical instrument showing portals for three implantable article deployment members.

FIG. 29 shows a surgical instrument having a vacuum element V and a plurality of portals 212, 213, and 214 for receiving implantable article deployment members.

Surgical instruments according to the present invention may include various features including cartridges, modular constructions, articulating distal portions and lockout features. For example, a lockout may be provided to block the implantation of an implantable article until the surgical device is properly deployed (e.g. for an embodiment with a balloon positioning member, the lockout may prevent implantation when the balloon is deflated). Another lockout may be provided that blocks the implantation unless a vacuum is generated. A different lockout may be provided that blocks movement of the implantable article deployment member if the surgical device is not loaded with an implantable article.

In another embodiment, the instrument may be adapted for use with a urethral sizer. The sizer may include a plurality of members adapted to be inserted in the urethra to approximate the size (diameter of the urethra). The surgical instrument may be modular in that it can include components (e.g. stabilizers and implantable article deployment members) of different sizes. The different sizes may be utilized to address the vagaries associated with the range of human anatomy sizes and shapes.

The surgical instruments may be manually powered, battery powered, motor driven or a combination or manual and motor driven or actuated. Additional surgical instruments and methods according to the present invention are described in U.S. provisional patent application No. 60/325,870, filed Sep. 28, 2001, and U.S. provisional patent application No. 60/316,552, filed Aug. 31, 2001.

The above-described surgical instruments may be disposable or reusable. Optionally, portions of the surgical instrument may be reusable (sterilizable) and other components may be disposable.

The surgical instruments, components thereof and sutures may be provided in a kit. The kit may include components for general surgical applications or it may be customized for a particular type of surgical procedure. Other accessories may also optionally be included in a kit according to the present invention. For example, a surgical drape specifically designed for urological procedures may be included in a kit of the present invention. Such a drape is disclosed in U.S. Published Pat. Appl. No. 2002/0078964 A1 published Jun. 27, 2002.

The individual elements of the kits of the present invention may be packaged together, separately or in subassemblies depending on a variety of factors such as shelf life and sterilization requirements. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), or plasma procedures.

Surgical Methods

In another aspect, the present invention comprises a surgical method. The surgical method may address general surgical disorders such as GERD, obesity or general tubular structure support. The tubular structure may comprise a natural passageway or one created by the surgical device.

The surgical procedure according to the present invention is particularly suitable for addressing a urological disorder such as incontinence. The urological disorders associated with the present invention include pelvic floor reconstruction or repair procedures. Examples of particular applications include, but are not limited to urinary incontinence treatment, paravaginal defect repairs, fecal incontinence treatment, repairs of cystoceles, rectoceles, and enteroceles, and prolapse repair.

In general, a method for treating a patient's incontinence comprises the steps of: (a) inserting a surgical device with an implantable article situated therein into a urethra, (b) moving the implantable article from a position within the urethra to a position at least substantially external to the urethra; (c) separating the implantable article from the device, and (d)

removing the surgical device from the urethra leaving the implantable article situated about the urethra. Preferably, in this embodiment, the incontinence is treated without requiring an incision in the vagina or abdomen of the patient.

In another embodiment of a method according to the present invention, the method for treating female urinary incontinence comprises the steps of: (a) providing a surgical device having an immobilizer and a stabilizer, and a implantable article deployment member movable about the immobilizer between a retracted position and an extended position; (b) inserting the immobilizer into the urethra and the stabilizer within the vagina; (c) moving the implantable article deployment member along a path that is substantially external to the urethra from the retracted to the extended position; (d) retracting the implantable article deployment member from the extended to the retracted position leaving the implantable article situated about the urethra; (e) separating the implantable article from the device; and (f) removing the surgical device from body. In this embodiment, the implantable article preferably treats the incontinence without substantially changing the patient's urinary tract orientation to avoid post implantation voiding difficulties.

General or local anesthesia may be utilized for the surgical procedures according to the present invention. In the case of incontinence procedures, it may be possible to conduct the surgical procedure under local anesthesia, have the patient stand just after the procedure and conduct a valsalva procedure or other test to determine the efficacy of the implantable article. This affords the surgeon the opportunity to tighten the implantable material about the urethra (e.g. if the patient remains incontinent) or loosen the implantable material (e.g. if the patient is in retention).

The nature of the present invention may also afford post surgical adjustment of the implantable material hours or perhaps days after the surgical procedure. For example, if the implantable article comprises a suture, the suture may be tied in an adjustable knot (e.g. a slip knot) to afford adjustment of the suture. Optionally, a portion of the suture may be left protruding from a vaginal incision for this purpose.

Unless otherwise specified, the present invention contemplates a variety of surgical approaches including transurethral, transperineal, transrectal, transvaginal, percutaneous, laparoscopic and combinations thereof.

All patents, patent applications, and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating a patient's incontinence comprising the steps of:
    inserting a surgical device with an implantable article situated therein into a urethra, wherein the implantable article is comprised of an elongate tubular tissue structure:
    moving the implantable article from a position within the urethra to a position a least substantially external to the urethra;
    separating the implantable article from the device; and
    removing the surgical device from the urethra leaving the implantable article situated about the urethra.

2. A method of treating incontinence according to claim 1 wherein the patient is female and the incontinence is treated without requiring an incision in the vagina or abdomen of the patient.

3. A method of treating female urinary incontinence comprising the steps of:
    providing a surgical device having an immobilizer and a stabilizer, and a implantable article deployment member movable about the immobilizer between a retracted position and an extended position;
    inserting the immobilizer into the urethra and the stabilizer within the vagina;
    moving the implantable article deployment member about the immobilizer from the refracted to the extended position thereby facilitating rotation of the implantable article adapted to cause penetration of urethral tissue and movement of the implantable article along a path that is substantially external to the urethra;
    retracting the implantable article deployment member from the extended to the retracted position leaving the implantable article situated about the urethra;
    separating the implantable article from the device; and
    removing the surgical device from the patient's body.

4. A method according to claim 3 wherein the implantable article treats the incontinence without substantially changing the patient's urinary tract orientation to avoid post implantation voiding difficulties.

* * * * *